United States Patent [19]
Phillipps et al.

[11] Patent Number: 5,392,781
[45] Date of Patent: Feb. 28, 1995

[54] BLOOD PRESSURE MONITORING IN NOISY ENVIRONMENTS

[75] Inventors: Patrick G. Phillipps, Lincoln; Paul Epstein, Brookline; David G. Tweed, Chestnut Hill, all of Mass.

[73] Assignee: CardioDyne, Incorporated, Brookline, Mass.

[21] Appl. No.: 686,420

[22] Filed: Apr. 16, 1991

[51] Int. Cl.$^6$ .............................................. A61B 5/0225
[52] U.S. Cl. .................................... 128/680; 128/682; 128/677; 364/413.03
[58] Field of Search ................................ 128/677–683, 128/672; 364/413.03

[56] References Cited

U.S. PATENT DOCUMENTS

| | | | |
|---|---|---|---|
| D. 297,260 | 8/1988 | Avoy et al. | D24/21 |
| 3,651,798 | 3/1972 | Egli et al. | 128/2.05 |
| 3,906,937 | 9/1975 | Aronson | 128/2.05 |
| 3,906,939 | 10/1975 | Aronson | 128/2.05 |
| 3,978,848 | 9/1976 | Yen et al. | 128/2.05 |
| 4,058,117 | 11/1977 | Kaspari et al. | 128/2.05 |
| 4,167,181 | 10/1979 | Lee | 128/682 |
| 4,216,779 | 8/1980 | Squires et al. | 128/682 |
| 4,245,648 | 1/1981 | Trimmer et al. | 128/680 |
| 4,261,368 | 4/1981 | Danna et al. | 128/680 |
| 4,262,674 | 4/1981 | Uemura et al. | 128/680 |

(List continued on next page.)

FOREIGN PATENT DOCUMENTS

| | | | |
|---|---|---|---|
| 0029349 | 5/1981 | European Pat. Off. | |
| 0256159 | 2/1988 | European Pat. Off. | |
| 0300354 | 1/1989 | European Pat. Off. | |
| WO88/04910 | 7/1988 | Japan . | |
| 2124906 | 7/1982 | United Kingdom | 128/680 |

OTHER PUBLICATIONS

D. Abelson, E. A. Kamens; Bedside measurement of systolic and diastolic time intervals using the stethometer; Cardiovascular Research, 1977, 11; pp. 270–274.

K. Bachmann, G. Bauerlein; Ambulatory Monitoring of Arterial Blood Pressure; Biotelemetry Patient Monitg 8; pp. 47–55; 1981.

M. W. Millar-Craig et al; Continuous Recording of Intra-Arterial Blood Pressure during Graded Bicycle Ergometry and Stair Climbind in Essential Hypertension; Biotelemetry Patient Monitg 8; pp. 33–46; 1981.

D. L. Stoner, T. H. Alexander, T. H. Alexander, Jr.; Blood Pressure Analysis During Treadmill Stress Testing; Journal of Clinical Engineering; vol. 4, No. 4; Oct.-Dec., 1979; pp. 369–371.

*Primary Examiner*—Lee S. Cohen
*Assistant Examiner*—Robert L. Nasser
*Attorney, Agent, or Firm*—Fish & Richardson

[57] ABSTRACT

Several techniques are provided for aiding in the discrimination of detected biological signals indicative of blood pressure from detected signals not indicative of blood pressure (e.g., noise). A threshold, based predominantly on a level of noise, is developed and used in the discrimination. A second threshold, based predominantly on levels of previously detected biological signals, is developed and additionally used to help discriminate the biological signals from noise. The biological signals are detected during a selected portion of a cardiac cycle, and additional signals detected outside of the selected portion of the cycle are applied to the detected signals. Another threshold may be developed based predominantly on a level of signals sensed by a transducer positioned to preferentially sense noise; the transducer is positioned so that the noise that it detects is related to noise that is detected during the detection of the biological signals. Blood pressure is measured during periodically scheduled measurement cycles, and a measurement cycle is suspended if noise exceeds a predetermined level. The times at which the detected signals (i.e., the signals indicative of blood pressure and the signals not indicative of blood pressure) are processed during a given cardiac cycle are selected based at least in part on the pressure of the cuff. The biological signals indicative of blood pressure that are detected during a current measurement cycle are used to at least in part determine the times at which the detected signals will be processed during a succeeding measurement cycle.

121 Claims, 8 Drawing Sheets

U.S. PATENT DOCUMENTS

| | | | |
|---|---|---|---|
| 4,295,471 | 10/1981 | Kaspari | 128/675 |
| 4,308,871 | 1/1982 | Shouda et al. | 128/686 |
| 4,356,827 | 11/1982 | Uemura et al. | 128/680 |
| 4,408,614 | 10/1983 | Weaver et al. | 128/680 |
| 4,417,587 | 11/1983 | Ichinomiya et al. | 128/682 |
| 4,461,266 | 7/1984 | Hood, Jr. et al. | 128/681 |
| 4,484,584 | 11/1984 | Uemura | 128/680 |
| 4,543,962 | 10/1985 | Medero et al. | 128/682 |
| 4,546,775 | 10/1985 | Medero | 128/681 |
| 4,561,447 | 12/1985 | Kawamura et al. | 128/687 |
| 4,566,463 | 1/1986 | Taniguchi et al. | 128/682 |
| 4,592,365 | 6/1986 | Georgi | 128/680 |
| 4,592,366 | 6/1986 | Sainomoto et al. | 128/680 |
| 4,617,937 | 10/1986 | Peel et al. | 128/680 |
| 4,627,440 | 12/1986 | Ramsey, III et al. | 128/682 |
| 4,638,810 | 1/1987 | Ramsey, III et al. | 128/681 |
| 4,660,567 | 4/1987 | Kaneko et al. | |
| 4,745,924 | 5/1988 | Ruff | 128/686 |
| 4,754,761 | 7/1988 | Ramsey, III et al. | 128/683 |
| 4,777,959 | 10/1988 | Wallach et al. | 128/677 |
| 4,841,980 | 6/1989 | Lee | 128/682 |
| 4,867,171 | 12/1989 | Yamaguchi | 128/680 |
| 4,889,132 | 12/1989 | Hutcheson et al. | 128/680 |
| 4,917,098 | 4/1990 | Murase | 128/677 |
| 4,938,227 | 7/1990 | Niwa et al. | 128/682 |
| 4,944,305 | 7/1990 | Takatsu et al. | |
| 4,953,557 | 9/1990 | Frankenreiter et al. | 128/677 |
| 4,967,756 | 11/1990 | Hewitt | 128/680 |
| 4,967,757 | 11/1990 | Frankenreiter | 128/682 |
| 5,014,714 | 5/1991 | Millay et al. | 128/680 |
| 5,054,495 | 10/1991 | Uemura et al. | 128/680 |
| 5,103,830 | 4/1992 | Shinomiya | 128/681 |

BLOOD PRESSURE MONITORING IN NOISY ENVIRONMENTS

BACKGROUND OF THE INVENTION

This invention relates to measuring blood pressure.

Systems for measuring blood pressure are generally known. During a measurement cycle, a blood pressure cuff secured around the patient's limb is inflated to a sufficiently high pressure to cut off arterial blood flow beneath the cuff, and the cuff is incrementally deflated to allow the artery to slowly open. As the cuff is deflated, biological signals indicative of blood pressure (such as sounds, known as Korotkoff sounds, caused by the blood forcing its way through the artery) are detected by a transducer on the cuff and converted to electrical signals that are processed to determine the systolic and diastolic blood pressures. This type of measurement technique is known as auscultation.

Other blood pressure measurement techniques are known. In oscillometry, small pressure changes in an inflated cuff induced by flowing blood are detected by a transducer (disposed either on the cuff or at a remote monitor) and used as a basis for determining blood pressure. Another procedure involves using multiple transducers to detect the times of occurrence of heart pulses at different locations along the artery, and determining the blood pressure based on the pulse propagation time between the transducers.

Often it is clinically useful to measure blood pressure (by any of the techniques described above, or possibly by other techniques) during critical care periods (for example, while the patient is undergoing surgery or being treating in an intensive care unit), or as the patient exercises to, for example, monitor how blood pressure changes with variations in heart rate. But activity, by the patient or by others, during these times generates noise (i.e., signals that are not indicative of blood pressure) that may be incorrectly interpreted, resulting in inaccurate blood pressure measurement.

In typical systems that measure blood pressure by auscultation, a threshold based on the level of previously received, valid Korotkoff sounds is applied to all signals produced by the transducer as a discriminant to remove noise. Some systems use two transducers that are spaced on the cuff to provide a half-period delay between the Korotkoff sounds and take the difference between the signals produced by the sensors to reinforce the Korotkoff sounds; because noise appears generally the same at each transducer, the noise level in the difference signal is reduced.

SUMMARY OF THE INVENTION

This invention, in general, employs numerous techniques used during the measurement of blood pressure for assisting the discrimination of biological signals (such as Korotkoff sounds) indicative of blood pressure from other signals not indicative of blood pressure (such as noise generated by the movement of the subject or by the activity of others that occur in all but the quietest measurement environments) and which, if not discounted, may result in erroneous measurements. The use of the techniques of this invention, separately or combined, leads to blood pressure measurements that are accurate and, equally as important, highly reliable even in high noise environments (such as those encountered with an exercising subject or when monitoring the subject in an operating room or an intensive care unit).

In one aspect, biological signals indicative of blood pressure and signals not indicative of blood pressure are detected and a threshold, based predominantly on a level of the signals which are not indicative of blood pressure, is developed and used to aid in discriminating the signals indicative of blood pressure from the signals not indicative of blood pressure.

In a related aspect, an additional, second threshold based predominantly on levels of previously detected signals indicative of blood pressure is developed and used to aid in the discrimination.

Preferred embodiments include the following features.

The signals are detected using at least one transducer and a blood pressure cuff, and the signals indicative of blood pressure include signals relating to blood flow (such as Korotkoff sounds). A pair of transducers (which may be separate devices or two areas of a single transducer) are disposed under an inflated blood pressure cuff to detect the signals.

The output signals generated by the transducers are summed together, which tends to reinforce the signals not indicative of blood pressure and reduce the signals indicative of blood pressure, thereby providing a useful indicator of the level of noise detected by the transducers. A fraction of the sum is used as the first-mentioned threshold. The fraction is adjusted based on heart rate. The first threshold is used for discrimination during successive cardiac cycles, and is developed for each cardiac cycle based on the signals not indicative of blood pressure detected during that cardiac cycle.

The output signals generated by the transducers are subtracted from each other to develop a candidate blood pressure signal in which the level of noise is reduced and the signals indicative of blood pressure are reinforced. Candidate blood pressure signals developed from signals previously detected by the transducers are averaged, and a fraction of the average is used as the second threshold. The candidate blood pressure signal is compared to the first and second thresholds, and thresholding is also applied to the signals produced by the individual transducers using a lower fraction of the average of the previously detected candidate blood pressure signals. The candidate is designated as a valid blood pressure signal if all of the thresholds are exceeded.

In another aspect, the biological signals indicative of blood pressure and the signals not indicative of blood pressure are detected during a portion of a cardiac cycle, and additional signals detected outside of the portion of the cardiac cycle are used to aid in the discrimination.

The portion of the cardiac cycle during which the biological signals are detected is, for example, a "cardiac gate" period. The additional signals occurring outside of the cardiac gate are likely to be noise (i.e., signals not indicative of blood pressure) rather than signals indicative of blood pressure, and thus these signals provide an accurate indication of the noise level that exists during the cardiac gate time. As a result, the thresholds can be adjusted if necessary for more accurate noise discrimination.

Preferred embodiments include the following features.

The fractions of the sum and of the difference used as the first and second thresholds are increased if the noise exceeds a predetermined level. This makes it more difficult for noise to exceed the thresholds and be erroneously designated as a valid blood pressure signal. The fractions are subsequently reduced (though not below minimum values) if the signals not indicative of blood pressure become less than the predetermined level. The noise is required to remain below the predetermined level for multiple cardiac cycles before the fractions are decreased to their original levels. The fractions are successively incremented for cardiac cycles in which the predetermined level is exceeded, and are successively decremented in smaller steps for cardiac cycles in which the predetermined level is not exceeded. Requiring noise level to remain low for multiple cardiac gates and incrementing the fractions in greater steps than those in which the fractions are decremented helps assure that the noise level has decreased meaningfully in both amplitude and duration before the thresholds are returned to nominal values. This further reduces the possibility that noise may be misinterpreted as a valid blood pressure signal.

Still another aspect of the invention is developing a threshold based predominantly on a level of signals sensed by a transducer positioned to preferentially sense signals that are not indicative of blood pressure, and using the threshold to aid in discriminating the signals indicative of blood pressure from the signals not indicative of blood pressure. Because the transducer is positioned to detect noise preferentially to blood pressure signals, this threshold provides an independent representation of the noise level.

Preferred embodiments include the following features.

The transducer is located remotely from the transducer (or transducers) used to detect the biological signals indicative of blood pressure and the signals not indicative of blood pressure. For example, the blood pressure transducers are disposed on or under cuff secured to a limb of the subject, and the transducer that preferentially detects noise is disposed elsewhere with respect to the subject (such as on a treadmill on which the subject is exercising). The threshold is developed based on signals sensed by the transducer during at least part of the cardiac gate. This provides a reliable indication of noise level on a gate-by-gate basis. The threshold is applied to the detected blood pressure signals together with the first-mentioned threshold and the second threshold. If all thresholds are exceeded, the detected signals are designated as valid blood pressure signals.

In a related aspect, the transducer is positioned so that it preferentially detects second signals not indicative of blood pressure and related to first signals not indicative of blood pressure that are detected during the detection of the biological signals; the second signals are used to aid in discriminating the biological signals (i.e., the signals indicative of blood pressure) from the first signals.

Preferred embodiments include the following features.

The biological signals indicative of blood pressure and the first signals are detected with a second transducer disposed on a cuff attached to a limb of the subject. The second transducer is positioned with respect to the cuff to be located near a blood vessel of the subject, and the first-mentioned transducer is positioned elsewhere on the cuff (or at another location on the subject) such that the first and second transducers pick up noise from the same source. As a result, the first and second signals are correlated.

A portion of the second signals are combined with the biological signals indicative of blood pressure and the first signals. The portion is selected to minimize the power of the biological signals indicative of blood pressure and the first signals. As a result, the level of the first signals not indicative of blood pressure is reduced with respect to that of the biological signals, thereby increasing the signal to noise ratio and further improving the noise discrimination.

Another aspect of the invention features a blood pressure measurement procedure in which the signals detected as a blood pressure cuff is being deflated are processed in each cardiac cycle by deriving a current candidate blood pressure signal based predominantly on the signals indicative of blood pressure detected during the current cardiac cycle, and comparing the candidate with a first threshold (based predominantly on a level of the signals not indicative of blood pressure detected during the current cardiac cycle) and a second threshold (based predominantly on candidate blood pressure signals detected during previous cardiac cycles) to aid in the discrimination; the candidate is deemed to be a validated blood pressure signal if it exceeds both thresholds; if the first threshold exceeds the candidate, the candidate is deemed ambiguous (i.e., it is possibly a blood pressure signal or noise); the candidate is designated as insignificant if it is exceeded by the second threshold.

Preferred embodiments include the following features.

For each cardiac cycle during which a validated blood pressure signal is determined to have occurred, the candidate blood pressure signal and a corresponding pressure of the cuff are stored, the cuff pressure is incrementally decreased, and the processing is repeated during a subsequent cardiac cycle. Because, particularly for systolic blood pressure measurement, "real" blood pressure signals (such as Korotkoff sounds) typically occur in successive cardiac cycles, a validated blood pressure signal is discarded unless another validated blood pressure signal occurs in a next subsequent cardiac cycle. This further reduces the risk that spurious noise will be mistaken for a true blood pressure signal.

Systolic pressure and diastolic pressure are determined from the stored candidate blood pressure signals and corresponding pressures by applying a third threshold to the stored candidate blood pressure signals, and designating as systolic pressure the highest stored pressure having a corresponding stored candidate blood pressure signal that exceeds the third threshold. The third threshold is derived based on the second threshold. Accordingly, if the second threshold is increased in response to the presence of high levels of noise, the third threshold is also increased. The third threshold is subsequently reduced with the second threshold if the noise abates.

To further aid in noise discrimination, a systolic pressure is rejected if it is not a predetermined amount lower than the initial pressure of the cuff. Systolic pressure is also rejected unless it is within a predetermined range of pressures based on previously measured systolic pressures for the subject, or if the systolic pressure has changed from a previously measured systolic pressure in a direction opposite to that in which the subject's heart rate has changed from a previous heart rate.

After systolic pressure has been determined, the cuff is deflated to a predetermined pressure above an expected diastolic pressure for the subject and blood pressure measurements are suspended during deflation. Because diastolic pressure typically does not change by large amounts, even when measured in several cycles, suspending measurement during the deflation poses little risk that a valid blood pressure signal will be overlooked. In fact, signals detected during deflation are more likely to be noise, and thus suspending measurement reduces the risk that the noise will be mistaken for valid blood pressure signals. Deflation can occur rapidly, thereby reducing the time needed to obtain the blood pressure measurement.

Then, the stored candidate blood pressure signals are analyzed to identify the candidate which occurred in a cardiac cycle that was followed by a predetermined number of cardiac cycles in which insignificant signals occurred. The stored pressure that corresponds to the identified blood pressure signal is designated as the diastolic pressure. The diastolic pressure is rejected unless it is within a predetermined range of pressures based on the average of previously measured diastolic pressures. This further assists in differentiating a true pressure measurement from spurious signals caused by noise.

If the threshold used to designate the systolic and diastolic pressures from the stored values is incremented due to the detection of high levels of noise, the designated systolic and diastolic pressures are incrementally changed based on the threshold increase. To avoid overcompensating, the total amount by which the systolic and diastolic pressures are changed is limited.

If the signal is determined to be ambiguous, the cuff pressure is kept constant and the processing is repeated during a subsequent cardiac cycle. If the ambiguity persists for a number of consecutive cardiac cycles, the cuff pressure is incrementally decreased and measurement continues at the lower pressure during the next cardiac cycle. This prevents the measurement from being stalled at a given pressure for an undue length of time.

If an insignificant signal is detected, the cuff pressure is incrementally lowered, and the measurement processes continues during a subsequent cardiac cycle at the new pressure.

The invention also features a computer assisted method of measuring blood pressure in which blood pressure is measured during each one of a number of periodically scheduled measurement cycles; during each cycle, biological signals indicative of blood pressure and signals not indicative of blood pressure are detected and processed, and the measurement cycle is suspended if signals not indicative of blood pressure exceed a predetermined level.

Preferred embodiments include the following features.

Measurement can be resumed during the cycle if the signals not indicative of blood pressure subsequently become less than the predetermined level. To avoid continual suspension in periods of prolonged noise, resumption is delayed for a predetermined interval after the predetermined level is no longer exceeded. Measurement recommences if the signals not indicative of blood pressure remain below the predetermined level for the entire interval. The measurement cycle is terminated if the accumulated time that measurement is suspended during the cycle exceeds a predetermined time. Measurement begins again in a subsequently-scheduled measurement cycle.

In another aspect of the invention, blood pressure measurement proceeds as a cuff is deflated from a predetermined pressure, and the detected signals (i.e., the signals indicative of blood pressure and the signals not indicative of blood pressure) are processed during successive cardiac cycles at times that are selected based at least in part on the pressure of the cuff.

Preferred embodiments include the following features.

The times are selected in accordance with the systolic pressure and the diastolic pressure being measured. More specifically, the times are based on a relationship between the pressure of the cuff and previously measured systolic and diastolic pressures. If cuff pressure exceeds the previously measured systolic pressure, the time is selected accordance with a time that corresponds to the previously measured systolic pressure. On the other hand, if cuff pressure is less than the previously measured diastolic pressure, the time is selected in accordance with a time that corresponds to the previously measured diastolic pressure. For intermediate pressures of the cuff, the time is selected by linear interpolation between the systolic time and the diastolic time based on the cuff pressure and the previously measured systolic and diastolic pressures.

In a related aspect, the blood pressure measurement is performed in a plurality of measurement cycles, and the biological signals indicative of blood pressure that are detected during the current measurement cycle are used to at least in part determine the times at which the detected signals will be processed during a succeeding measurement cycle.

Preferred embodiments include the following features.

The selected times each represent a time delay between a predetermined event in a cardiac cycle (such as an R-wave) and a timing signal representing biological signals indicative of blood pressure (such as a Korotkoff sound). Systolic and diastolic pressures are determined by identifying the timing signals from detected signals, and the times for a subsequent blood pressure measurement based on said time delays for said timing signals. The times for succeeding measurement cycles are changed if the time delays that actually occurred differ from the times used during the current measurement cycle. The times for the succeeding measurement cycle are also selected based on changes in heart rate of the subject.

By adaptively changing the times at which the detected signals are processed, both during a measurement cycle and in successive measurement cycles, the times at which the signals are examined for the presence of biological signals indicative of blood pressure are tailored to those periods during which the biological signals are most likely to occur. Signals occurring during other times are ignored, and as a result the discrimination of valid blood pressure signals from noise is significantly enhanced.

Other features and advantages of the invention will become apparent from the following detailed description, and from the claims.

DESCRIPTION OF THE PREFERRED EMBODIMENTS

We first briefly describe the drawings.

STRUCTURE AND OPERATION

1. Operational Overview

Figure 1:
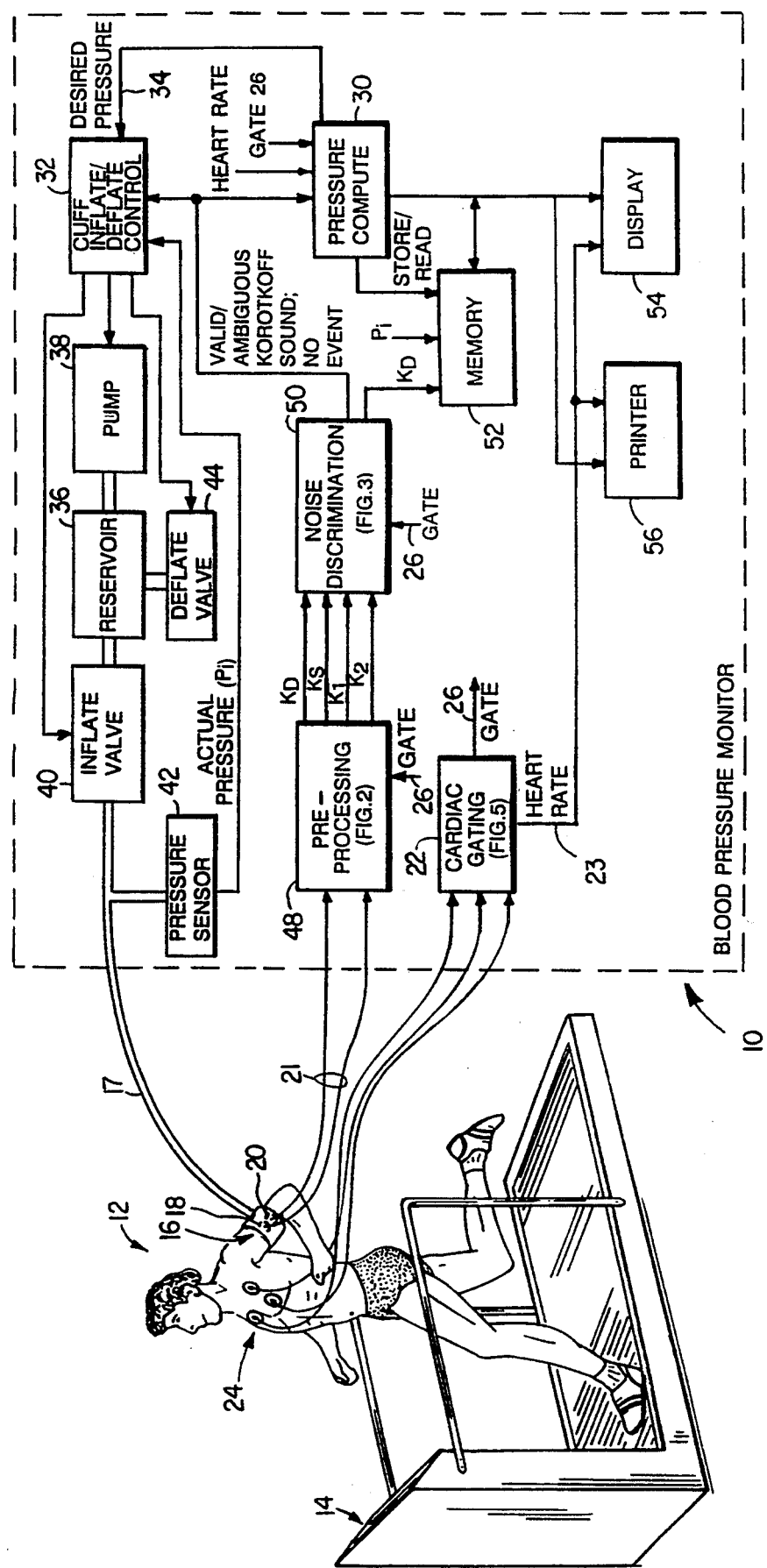
FIG. 1 shows the blood pressure monitor of this invention in use with an exercising patient.

Referring to FIG. 1, blood pressure monitor 10 employs numerous techniques described in detail below for discriminating valid blood flow signals (i.e., Korotkoff sounds) from noise and other spurious signals that are typically encountered in all but the quietest environments and which, if not removed, may render the blood pressure measurement inaccurate (or, in some cases, impossible to make). The noise may be caused by the motion of patient whose blood pressure is being monitored or may be the result of activity by others, such as nearby health care providers. Thus, while patient 12 is shown exercising or undergoing a stress test on treadmill 14, the patient may alternatively be exercising in another fashion or be resting and prone and receiving care in such areas as an operating room or an intensive care unit.

Monitor 10 measures blood pressure by the auscultation technique and includes a blood pressure cuff 16 equipped with a pair of spaced, independent transducer sensing areas 18, 20 (which may comprise two portions of one transducer or a pair of transducers) each of which is connected to blood pressure monitor 10. Transducers 18, 20 are disposed under cuff 16, but other arrangements may be used instead. Cardiac gating circuitry 22 monitors the heart functions of patient 12 in a manner described in detail below with a set of cardiac electrodes 24 (only three of which are shown), and provides a gate 26 for each heart period during which signals from transducers 18, 20 are analyzed to determine the presence or absence of Korotkoff sounds. Transducer signals are also analyzed outside of the cardiac gate time to quantify noise for use in the discrimination process.

Briefly, blood pressure measurement proceeds as follows. Measurements are made cyclically, such as every one to five minutes, under the control of a pressure computer 30. At the start of each cycle, computer 30 triggers cuff controller 32 to inflate cuff 16 via hose 17 to a desired pressure 34. (Desired pressure 34 is established by performing an initial blood pressure measurement, as described below, and is approximately 25 mm Hg above the systolic pressure obtained during the initial measurement.) Cuff controller 32 fills reservoir 36 by activating pump 38 and then opens valve 40 to rapidly inflate cuff 16. Sensor 42 monitors the actual pressure ($P_i$) of cuff, digitizes the pressure measurement, and provides it to controller 32. Cuff controller 32 activates pump 38 and valve 40, and if necessary deflate valve 44, to maintain $P_i$ at the desired value.

Transducers 18, 20 detect biological signals (such as Korotkoff sounds) that are indicative of blood pressure as well as signals (such as noise) that are not indicative of blood pressure, and convert these signals to electrical signals. At the occurrence of each cardiac gate 26, the electrical signals from transducers 18, 20 are preprocessed (48) and applied to a noise discrimination procedure (50). Preprocessing (48) and noise discrimination (50) are described in detail below. Suffice it here to say that they implement computer programs executed by a microprocessor (not separately shown) to determine, for each gate 26, whether transducers 18, 20 have detected a valid Korotkoff sound or an ambiguous sound, or whether essentially no sounds (i.e., insignificant sounds) have been detected. If a valid Korotkoff sound is detected, computer 30 saves the signal level of the Korotkoff sound ($K_D$) and the pressure ($P_i$) in memory 52 and signals cuff controller 32 to incrementally deflate (such as by 3 mm Hg) cuff 16 by momentarily opening valve 44. Computer 30 also triggers cuff controller 32 to incrementally deflate cuff 16 if only low level sounds (too small to qualify as Korotkoff sounds or disrupt measurement) are detected, but does not save either $K_D$ or $P_i$. If noise (i.e., an ambiguous sound) is detected, computer 30 causes cuff controller 32 to maintain the cuff pressure at its present level, and the processing of new signals from transducers 18, 20 is repeated upon the occurrence of the next cardiac gate 26.

As described in detail below, after a number of (such as five for the initial measurement cycle and two for subsequent cycles) Korotkoff sounds $K_D$ have been saved in memory 52, computer 30 determines which saved Korotkoff sound $K_D$ represents the systolic component of the patient's blood pressure and designates the pressure $P_i$ associated with that Korotkoff sound as a candidate for the systolic pressure. Computer 30 executes a number of routines to validate the candidate systolic pressure based on such factors as the previously measured, valid systolic pressure, the heart rate of patient 12, and the initial cuff inflation pressure. If the candidate systolic pressure is determined to be invalid, it is discarded, and computer 30 signals cuff controller 32 to reinflate cuff 16 for remeasurement. The candidate systolic pressure located during the remeasurement is accepted.

If the candidate systolic pressure is determined to be valid, computer 30 signals cuff controller 32 to rapidly deflate cuff 16 to a pressure that is 15 mm Hg above the previously (or initially) measured diastolic pressure. This avoids the need for making measurements at pressures that probably are above the diastolic pressure of patient 12, thereby saving significant time in the measurement cycle and reducing the possibility that noise will be measured at such intermediate pressures.

Signals from transducers 18, 20 continue to be preprocessed (48) and discriminated (50) from noise during each cardiac gate 26. As with systolic pressure measurements, valid Korotkoff sound signals $K_D$ and the pressures $P_i$ at which they are measured are stored in memory 52, cuff 16 is incrementally deflated, and measurements are taken again at the new pressure. Cuff 16 is also incrementally deflated after each cardiac gate 26 during which no Korotkoff sounds were measured, and measurements are taken at each new pressure. If noise (i.e., an ambiguous sound) is detected during gate 26 in a given heart period, the pressure $P_i$ of cuff 16 is held constant and the measurement is repeated at the next cardiac gate 26.

As the cuff pressure is reduced, the pressure on the artery of the patient will eventually fall to a level at which the Korotkoff sounds cease altogether. When computer 30 determines that two consecutive cardiac gates 26 have occurred in the absence of valid Korotkoff sounds and the current pressure of cuff 16 is below the average diastolic pressure, computer 30 designates the stored pressure $P_i$ associated with the most recently saved Korotkoff sound $K_D$ as the diastolic component of blood pressure. Cuff controller 32 is then triggered to fully deflate cuff 16. The systolic and diastolic blood pressure measurements are saved in memory 52 and used to validate the systolic and diastolic pressures measured in the next cycle. The current systolic and diastolic pressures are sent (together with present heart rate 23) to display 54 for presentation to the user. These values and other patient data are periodically sent to printer 56 to obtain a history of these functions.

2. Preprocessing and Noise Discrimination

Figure 2:
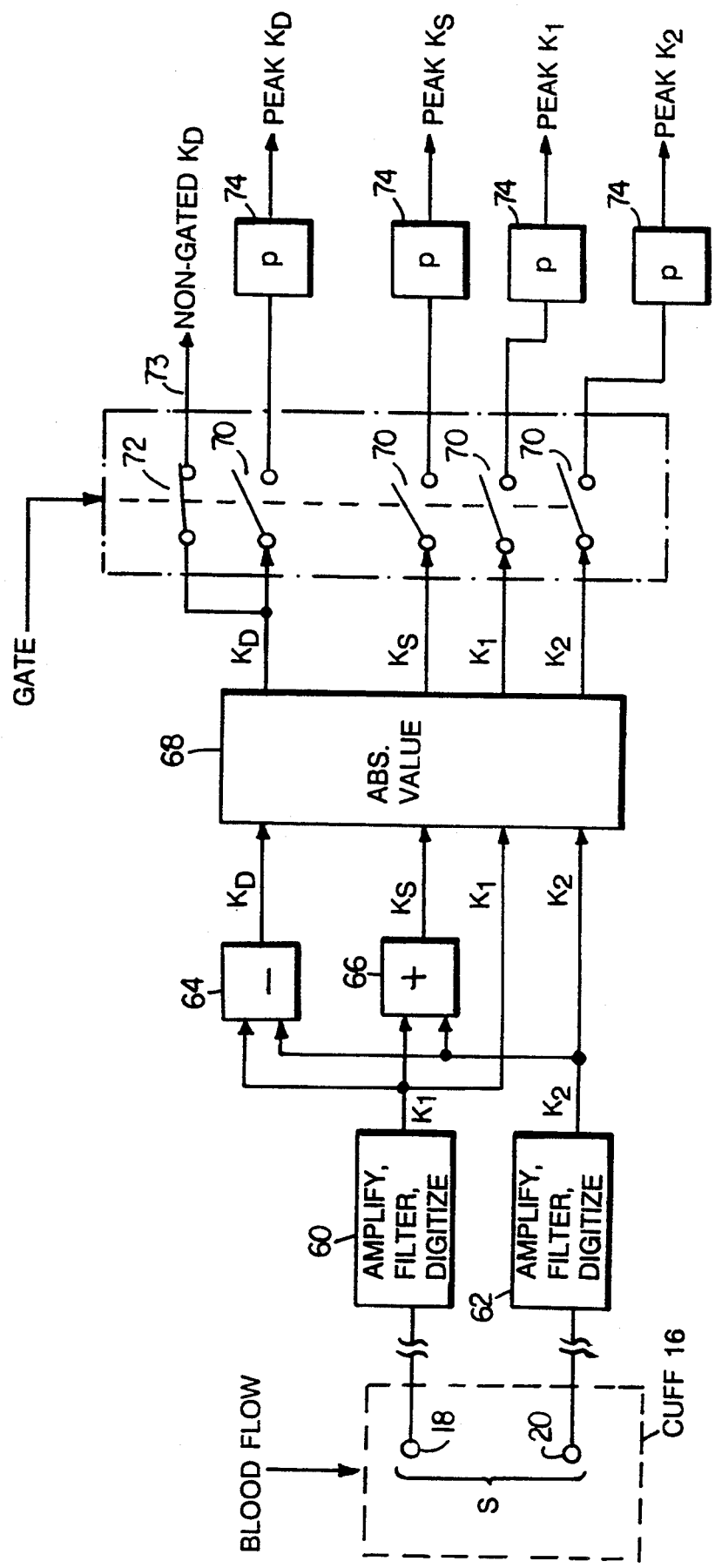
FIG. 2 depicts a portion of the blood pressure monitor of FIG. 1 that initially processes the signals from the blood pressure cuff transducers.

Referring to FIG. 2, blood pressure cuff transducers 18, 20 are spaced on cuff 16 so that transducer 20 lies downstream (i.e., distally) of transducer 18 over an artery in the limb. While Korotkoff sounds are periodic in nature and propagate at a finite speed down the length of the artery, noise is usually nonperiodic and typically appears essentially the same at different points along the artery. The spacing S between transducers 18, 20 is chosen so that transducer 20 detects Korotkoff sounds that are delayed by approximately one-half period (i.e., 180 degrees) with respect to the Korotkoff sounds detected by transducer 18, subject to patient variations. For example, spacing S is 0.5 inches. Most noise is detected substantially identically by both transducers 18, 20.

Transducers 18, 20 convert the sounds that they receive (both Korotkoff sounds and noise) to electrical signals and transmit the signals via cable 21 to respective input stages 60, 62 of preprocessor 48. There, the signals are amplified, bandpass filtered (to remove signal frequencies that are known to be outside of the possible frequency range for Korotkoff sounds) and digitized (i.e., by standard analog-to-digital conversion techniques). The outputs of input stages 60, 62 (corresponding respectively with proximal and distal transducers 18, 20) will be identified below as $K_1$ and $K_2$, although it is understood that these signals may represent valid Korotkoff sounds, ambiguous sounds (i.e., noise) or low-level sounds that are neither blood flow sounds or noise.

A subtracter 64 takes the difference between proximal transducer signal $K_1$ and distal transducer signal $K_2$ to produce a difference signal $K_D$. Transducer signals $K_1$ and $K_2$ are summed together in adder 66 to generate a sum signal $K_S$. Because of the one-half period delay between the Korotkoff sounds as detected by transducers 18, 20, the Korotkoff sounds are reinforced in difference signal $K_D$ and substantially canceled from the sum signal $K_S$. But because noise appears essentially the same to transducers 18, 20, the noise is reinforced in sum signal $K_S$ and substantially attenuated in difference signal $K_D$. Thus, the amplitude of difference signal $K_D$ represents that of a candidate Korotkoff sound, and sum signal $K_S$ has an amplitude is used to provide a noise threshold for Korotkoff signal $K_D$.

The absolute values of sum and difference signals $K_S$, $K_D$ and the individual transducer signals $K_1$, $K_2$ are taken (68) to provide signals that are always positive for subsequent processing. Then, the signals are applied to a set of switches 70, 72 that are controlled by cardiac gate 26. Cardiac gate 26 closes switches 70 only during a predetermined interval of each heart period during which the Korotkoff sounds are most likely to occur. This helps prevent noise detected by transducers 18, 20 between gates 26 from erroneously being interpreted as Korotkoff sounds. As discussed in detail below, one of the features of this invention is adaptively changing the timing and duration of cardiac gate 26 in accordance with such factors as the previously measured systolic and diastolic blood pressures and changes in the heart rate of the individual patient. The state of switch 72 is maintained opposite to that of switches 70 (i.e., switch 72 is closed only between cardiac gates 26) to provide a non-gate time $K_D$ signal 73 used (as described in detail below) to determine if the environment is unusually noisy.

During each gate 26, a set of detectors 74 determines the peak values of difference signal $K_D$, sum signal $K_S$, and individual transducer signals $K_1$ and $K_2$. Noise discrimination (50) is performed on the basis of these four peak values.

Figure 3:
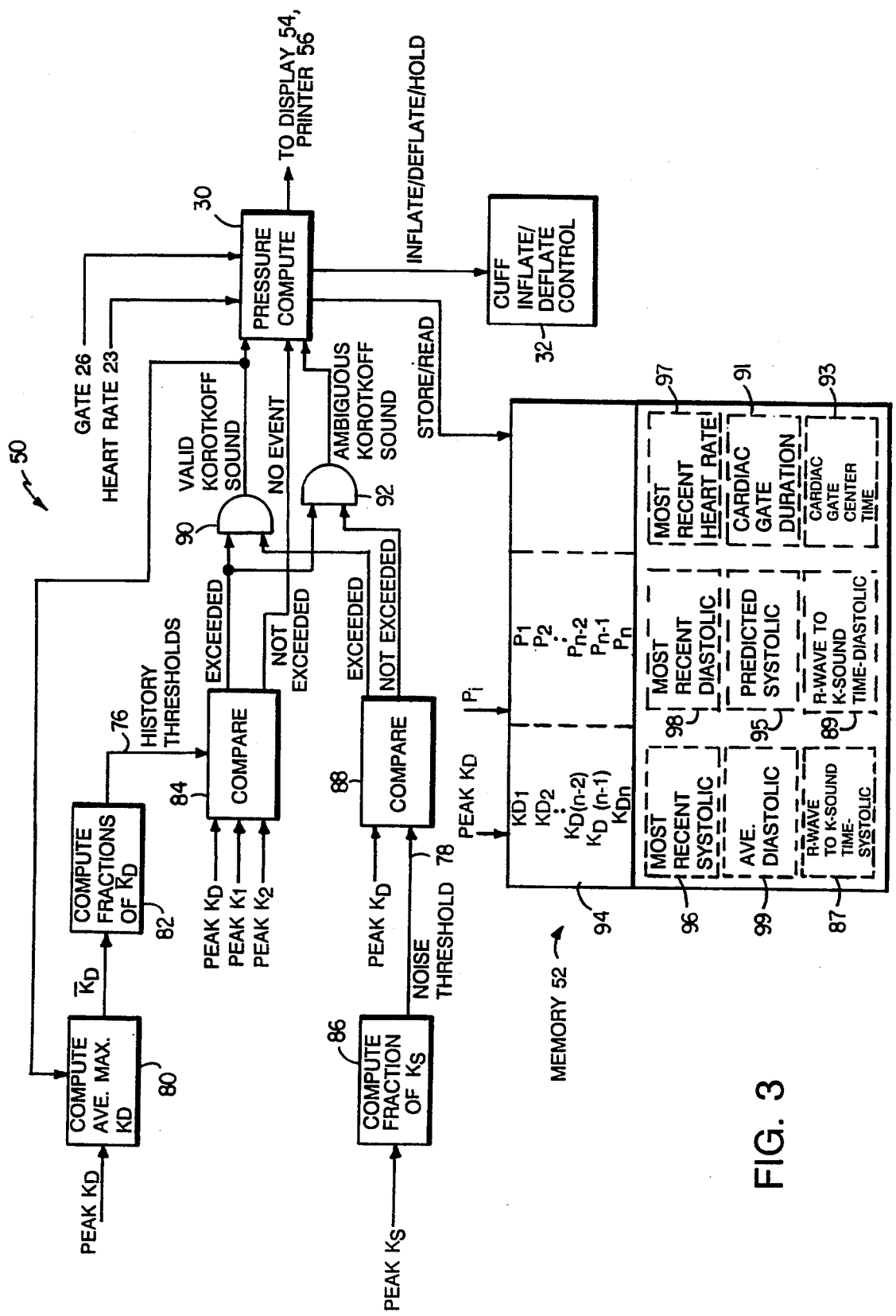
FIG. 3 shows discriminating the blood pressure signals from noise in another portion of the blood pressure monitor of FIG. 1.

FIG. 3 is a detailed functional block diagram of the preferred noise discrimination process (50). In general, noise discrimination (50) includes two thresholding steps, each of which must be satisfied in order for a candidate Korotkoff sound (i.e., peak $K_D$) to be considered valid. First, the candidate Korotkoff sound (peak $K_D$) and the individual transducer signals (peak $K_1$ and peak $K_2$) must all have amplitudes that exceed thresholds 76 ($K_D$ thresholds) based on the history of previously received, valid Korotkoff sounds. The amplitude of the candidate Korotkoff sound (peak $K_D$) must also exceed a noise threshold 78 that is derived from the sum signal (i.e., peak $K_S$). If all thresholds are exceeded the candidate Korotkoff sound is accepted by computer 30 as valid and stored (together with the pressure $P_i$ at which the sound was measured) in memory 52.

History thresholds 76 are derived from the average maximum amplitude ($\overline{K_D}$) of the difference signals (i.e., the peak $K_D$ signals) that have been received and determined to represent valid Korotkoff sounds (80). (A preset value representative of the amplitude of a normal Korotkoff sound is used as the average maximum amplitude ($\overline{K_D}$) for the initial measurement cycle; the preset value is updated after the initial cycle as described below.) Computer 30 derives (82) history thresholds 76 by computing fractions of the average maximum amplitude $\overline{K_D}$ and performs a comparison (84) between the peak $K_D$, $K_1$, and $K_2$ signals in each gate 26 and history thresholds 76.

The history threshold 76 with which peak $K_D$ is compared is 25% of the average maximum amplitude $\overline{K_D}$. Because Korotkoff sounds are reinforced in $K_D$, the amplitude of $K_D$ should exceed that of $K_1$, and $K_2$, and consequently a lower history threshold 76 is used for $K_1$ and $K_2$. The history threshold with which $K_1$ and $K_2$ are compared is ¼ of the history threshold used for $K_D$ (i.e., 6.25% of the average maximum amplitude $\overline{K_D}$). A candidate Korotkoff sound detected in a given cardiac gate 26 satisfies the history thresholding only if the peak $K_D$, $K_1$, and $K_2$ signals all exceed their respective thresholds 76.

Noise threshold 78 changes on a cardiac gate-by-gate basis. That is, the noise threshold used for a candidate Korotkoff sound detected in a given cardiac gate 26 is based upon the sum signal (i.e., peak $K_S$) that was detected during that gate 26. Noise threshold 78 is computed (86) to be 83% of the peak $K_S$ for heart rates less than 120 beats per minute; for greater heart rates, 100% of $K_S$ is used. Noise threshold 78 is compared (88) with the candidate Korotkoff sound (i.e., peak $K_D$), and the candidate sound is discarded as noise unless it exceeds noise threshold 78.

The results of comparisons 84, 88, as well as combinations of these results, are used to determine whether a valid Korotkoff sound, an ambiguous sound (i.e., noise), or no event occurred during a cardiac gate. Specifically, if less than all of the $K_D$, $K_1$, and $K_2$ signals exceed history thresholds 76, the sounds detected by transducers 18, 20 in the current cardiac gate 26 are deemed to be of insufficient amplitude to represent Korotkoff sounds. Computer 30 responds by triggering cuff controller 32 to incrementally deflate cuff 16, and new transducer signals are again measured at the new pressure $P_i$ upon the occurrence of the next cardiac gate 26.

If history thresholds 76 are all exceeded and noise threshold 78 is exceeded, the candidate Korotkoff sound that occurred during the current cardiac gate 26 is deemed to be valid (this operation is shown by logic AND gate 90). Computer 30 responds by storing the corresponding peak $K_D$ and the blood pressure $P_i$ at which the candidate Korotkoff sound was measured together in a table 94 in memory 52. The peak $K_D$ is also used to update the average maximum amplitude ($\overline{K_D}$) 80. Computer 30 triggers cuff controller 32 to incrementally deflate cuff 16, and the measurements are repeated during the next cardiac gate 26.

On the other hand, if history thresholds 76 are all exceeded but the candidate Korotkoff sound is not greater than noise threshold 78, the candidate Korotkoff sound is ambiguous and is deemed to be noise (this operation is denoted by logic AND gate 92). The blood pressure measurement at the current pressure $P_i$ is thus ambiguous, and computer 30 directs controller 32 to hold cuff pressure $P_i$ at its current level. Measurement of the signals produced by transducers 18, 20 and noise discrimination 50 are repeated for this pressure during the next cardiac gate 26. If the noise level has abated by this time (as often occurs) then the result of noise discrimination 50 will be either a "no event" (history thresholds not all exceeded) or a valid Korotkoff sound; if so, computer 30 proceeds as discussed above.

At times, the noise level will not have abated by the time that the next cardiac gate occurs. In that case, computer 30 again causes cuff controller 32 to maintain the pressure of cuff 16 at its current level, and the measurement and noise discrimination steps are repeated at the next cardiac gate. If ambiguous sounds appear during a predetermined number of (such as four) consecutive cardiac gates 26, computer 30 incrementally deflates cuff 16 and measures and analyzes signals from transducers 18, 20 at the new pressure $P_i$ during the next cardiac gate 26. This prevents the blood pressure measurement from being suspended indefinitely during prolonged periods of high noise.

Occasionally, noise may be incorrectly designated as a valid Korotkoff sound and stored (with the associated pressure) in memory 52. It is unlikely, however, that this will occur over a number of consecutive cardiac gates 26. Thus, during systolic blood pressure measurement, computer 30 determines whether a valid Korotkoff sound (as designated by AND gate 90) detected in a given cardiac gate 26 is followed by a valid Korotkoff sound in one of the next two cardiac gates 26. If not, the Korotkoff sound is reclassified as invalid and is discarded as an isolated event (such as noise) that does not accurately represent systolic pressure.

Each time that a $K_D$-$P_i$ pair is validated as discussed above, it is stored in memory table 94 and computer 30 determines the number of pairs that have been saved. For the initial blood pressure measurement, when five $K_D$-$P_i$ pairs have been stored computer computes a new value for the average maximum $\overline{K_D}$ from the four largest values of $K_D$ in table 94. (This new average maximum value will be used to generate history thresholds 76 during the next measurement cycle.) Computer 30 then scans the stored $K_D$ values in the order in which they have been stored (i.e., $K_{D1}$, $K_{D2}$, $K_{D(n-2)}$, $K_{D(n-1)}$, $K_{Dn}$) and compares each $K_D$ value with a fraction (25%) of the new average maximum $\overline{K_D}$. The pressure $P_i$ that is associated in table 94 with the first $K_D$ value that exceeds this fraction is selected as a candidate for the systolic pressure of the patient.

In subsequent measurement cycles, computer scans the $K_D$ values stored in table 94 for that measurement after only two $K_D$-$P_i$ pairs have been stored. The first-saved $K_D$ value that exceeds 25% of the average maximum $\overline{K_D}$ used during the measurement cycle becomes the candidate systolic pressure. Upon completion of the measurement cycle (i.e., after valid systolic and diastolic pressures have been determined), computer 30 recalculates the average maximum $\overline{K_D}$ 80 for use during the next measurement cycle using up to four largest values of $K_D$ from table 94. Table 94 is cleared after each measurement cycle.

Computer 30 does not accept a candidate systolic pressure unless it is at least 20 mm Hg below the initial cuff inflation pressure. Moreover, before accepting the candidate systolic pressure, computer 30 compares it with a predicted systolic pressure (stored in location 95) that is based on the most recently measured, valid systolic pressure 96 (i.e., as determined in previous measurement cycle) and the heart rate 97 at which it was measured, both of which are stored in memory 52. Predicted systolic pressure 95 equals most recent systolic pressure 96 plus (or minus) the change in heart rate from that of the previous measurement cycle 97. If the candidate systolic pressure differs from predicted systolic pressure 95 by more than +20 mm Hg or −20 mm Hg, the candidate is rejected. Additionally, if the candidate systolic pressure changes in a direction opposite to the direction in which the heart rate has changed (e.g., systolic pressure decreases despite an increase in heart rate—which indicates that patient 12 may be in distress) the candidate is rejected. Whenever the candidate systolic pressure is rejected, cuff 16 is reinflated, and the measurement procedure is repeated one more time. (If the candidate is rejected for being less than 20 mm Hg below the initial cuff pressure, a new, higher cuff pressure is used.) The candidate systolic pressure obtained during the remeasurement is accepted.

If the candidate systolic pressure passes the above tests, it is accepted and becomes the most recent systolic pressure 96. Predicted systolic pressure 95 and most recent heart rate 97 are updated accordingly. The systolic pressure is also sent to display 54 and printer 56. Cuff controller 32 rapidly deflates cuff 16 to a pressure that is 15 mm Hg above the average diastolic pressure 99 (i.e., as determined in previous measurement cycles).

Noise discrimination 50 operates during the measurement of the diastolic pressure in the same manner as described above. If a valid Korotkoff sound is detected in a cardiac gate, the corresponding $K_D$-$P_i$ pair is stored in memory table 94 and cuff 16 is incrementally deflated. If no event is detected in a cardiac gate 26, the corresponding $K_D$-$P_i$ values are not stored, but cuff 16 is incrementally deflated. If an ambiguous sound is detected, cuff pressure is maintained and the analysis of the transducer signals is repeated for up to four consecutive cardiac gates in an attempt to obtain a valid measurement (i.e., Korotkoff sound or "no event") for that pressure, as discussed above.

Measurement continues until computer 30 determines that a valid Korotkoff sound during one cardiac gate 26 has been followed by two consecutive cardiac gates 26 in which no event (i.e., neither a valid Korotkoff sound nor noise) has occurred and the cuff pressure is below an average 99 of previously measured, valid diastolic pressures. The pressure $P_i$ that corresponds to that last valid Korotkoff sound is selected as a candidate diastolic pressure. The average diastolic pressure of a patient typically changes little over time, even if other parameters such as heart rate change significantly. Thus, before a candidate diastolic pressure is accepted as valid, it is compared to the stored average diastolic pressure 99. If the candidate differs from average 99 by more than +/−25 mm Hg, the candidate is discarded and the average diastolic pressure 99 is used (and displayed) instead.

Average diastolic pressure 99 is maintained during the next measurement cycle. However, if the candidate diastolic pressure developed during the next cycle also differs by more than +/−25 mm Hg from average 99, the systolic and diastolic measurement cycle is aborted. All parameter values are reset to their start-up levels and the blood pressure measurement procedure is restarted with a new initial measurement cycle.

When a candidate diastolic pressure is accepted, computer 30 sends the new pressure to display 54 and printer 56 for presentation to the user. The stored values for most recent diastolic pressure 98 and average diastolic pressure 99 are updated accordingly. Average diastolic 99 is updated by adding the previous average to the diastolic pressure obtained in the current measurement cycle and dividing the result by two. Cuff 16 is then fully deflated. The entire systolic and diastolic measurement and validation procedure is repeated in the next, regularly scheduled measurement cycle. Table 94 is cleared at the start of the next measurement cycle, but the stored values for predicted systolic pressure 95, most recent systolic pressure 96, most recent heart rate 97, most recent diastolic pressure 98, and average diastolic pressure 99 are maintained and used during the next measurement cycle.

3. Adjustment of Thresholds for Noisy Environments

Figure 4:
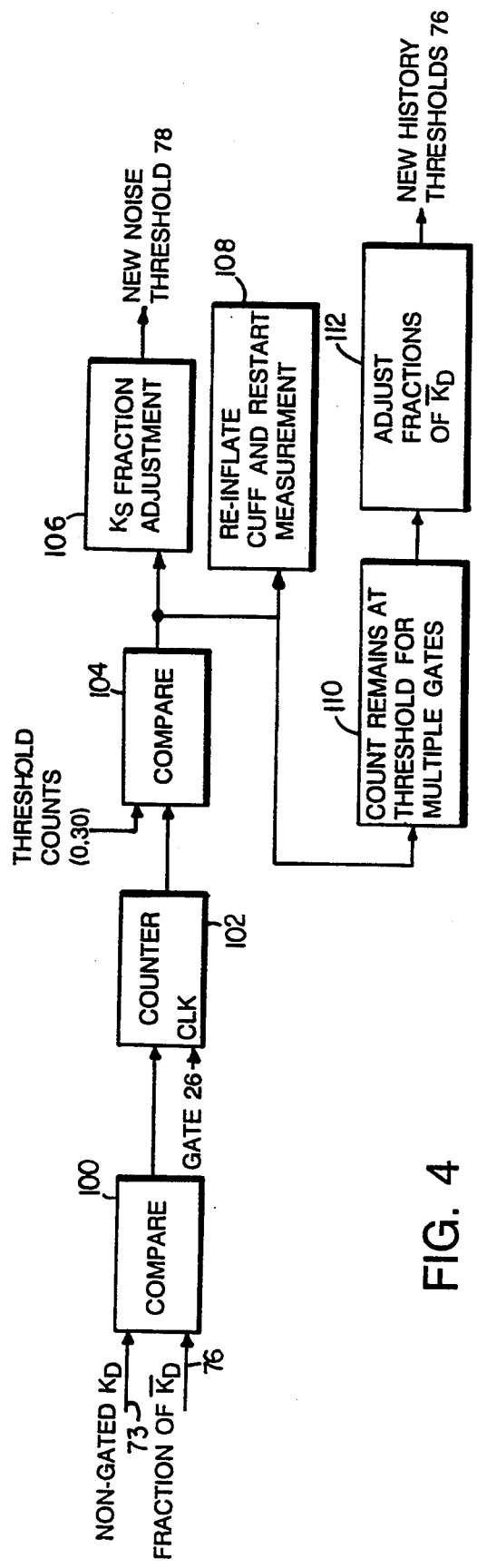
FIG. 4 shows adjusting one of the noise thresholds of FIG. 3 in a particularly noisy environment.

Referring also to FIG. 4, computer 30 adaptively adjusts the amplitudes of history thresholds 76 and noise threshold 78 according to the noise level so that particularly high levels of noise detected by transducers 18, 20 will be less likely to be erroneously designated as valid Korotkoff sounds. The noise level is determined by comparing (100) the amplitude of difference signal $K_D$ outside of each cardiac gate (i.e., non-gate time $K_D$ signal 73) with $K_D$ history threshold 76. As discussed above, $K_D$ history threshold 76 is 25% of the stored maximum average $\overline{K_D}$ 80. If the threshold is exceeded, a counter 102 (initially set to a count of 10) is incremented by 10 at the start of the next cardiac gate 26. Otherwise, counter 102 is decremented by two when the next cardiac gate 26 occurs. The maximum count of counter 102 is thirty; the minimum count is zero.

The count is compared (104) to a threshold value of 30, and if the count reaches the threshold, computer 30 increases (106) the fraction of $K_S$ which will be used as noise threshold 78 in the next cardiac gate 26. As discussed above, the initial fraction of $K_S$ is 83% for heart rates below 120 beats per minute and is 100% otherwise. The first time that counter 102 reaches a count of 30, computer 30 increases these fractions to 150% of $K_S$. At this amplitude, noise threshold 78 should exceed most noise levels. Cuff controller 32 is directed to reinflate cuff 16 to the initial pressure (106), and the measurement cycle is restarted (108).

If the noise level remains high after the next cardiac gate 26, comparator 100 will indicate that the non-gated $K_D$ signal still exceeds the threshold, and counter 102 will not be decremented. Counter 102 thus continues to hold a count of thirty (110). Computer 30 responds by increasing the history thresholds 76 to which the peak $K_D$, $K_1$, and $K_2$ signals are compared, as well as the $K_D$ threshold used to designate systolic and diastolic pressures from table 94, by 20% for the next cardiac gate 26 (112). This makes it more difficult for noise to qualify as an event, thereby further lowering the possibility that the noise will erroneously be deemed to be a Korotkoff sound and that the displayed systolic and diastolic pressures will be erroneous. Computer 30 successively increments history thresholds 76 by 20% for each subsequent cardiac gate 26 that follows a non-gate period in which the count of counter 102 remains at thirty.

Increases in the $K_D$ threshold used to designate systolic and diastolic pressures from table 94 may result in a pressure lower than the patient's true systolic pressure and a pressure higher than the true diastolic pressure to be designated as systolic and diastolic pressures. To avoid erroneous results, computer 30 compensates by increasing the systolic pressure and lowering the diastolic pressure obtained from table 94 by 1 mm Hg for each 10% increase in the $K_D$ threshold. The maximum amount that computer 30 is permitted to adjust the pressures in a measurement cycle is 8 mm Hg.

Of course, the increases in history thresholds 76 and noise threshold 78 may result in valid Korotkoff sounds being temporarily designated as noise and ignored. However, as discussed above, whenever an ambiguous sound is detected, the current cuff pressure is maintained and the signals produced by transducers 18, 20 are simply re-analyzed during the next cardiac gate 26. Often, the noise level will subside sufficiently so that history thresholds 76 and noise threshold 78 will have been decreased (as discussed below) within a few cardiac gates, and thus the "real" Korotkoff sounds are validated with only a slight delay. However, to prevent indefinite suspension of the blood pressure measurement, computer 30 aborts the measurement cycle if the history threshold 76 used for the peak $K_D$ signal (i.e., the threshold that is initially set at 25% of the average maximum $\overline{K_D}$) reaches 150% of the average maximum $\overline{K_D}$. Cuff 16 is completely deflated, and computer 30 discards all of the Korotkoff values and systolic and diastolic pressure data in memory 52. Measurement begins anew at the start of the next scheduled measurement cycle.

If the noise level decreases below the threshold value of $K_D$ after a cardiac gate 26, the count of counter 102 is lowered by two (such as to 28). Computer 30 refrains from making further increases in history thresholds 76 for the next gate 26, but does not immediately decrease history thresholds 76 or noise threshold 78. Instead, thresholds 76, 78 are maintained at their current levels until the noise level has remained below the threshold for a number of cardiac gates sufficient to allow counter 102 to be decremented to zero. When counter 102 reaches zero, computer 30 re-adjusts history threshold 78 to its initial percentage of $K_S$ and lowers by 5% noise thresholds 76 (including the $K_D$ thresholds used to locate systolic and diastolic pressures from table 94). If the count remains at zero after subsequent cardiac gates 26, these history thresholds 76 are lowered in 5% increments until they regain their initial levels. Because the value of counter 102 and the levels of noise thresholds 76 are increased (in response to high noise levels) by a much greater amount than they are decreased (in response to low noise levels), a single high-level noise event results in the use of higher thresholds for several subsequent cardiac gates 26. This feature provides the blood pressure measurement with still greater noise immunity.

4. Cardiac Gating

Figure 5:
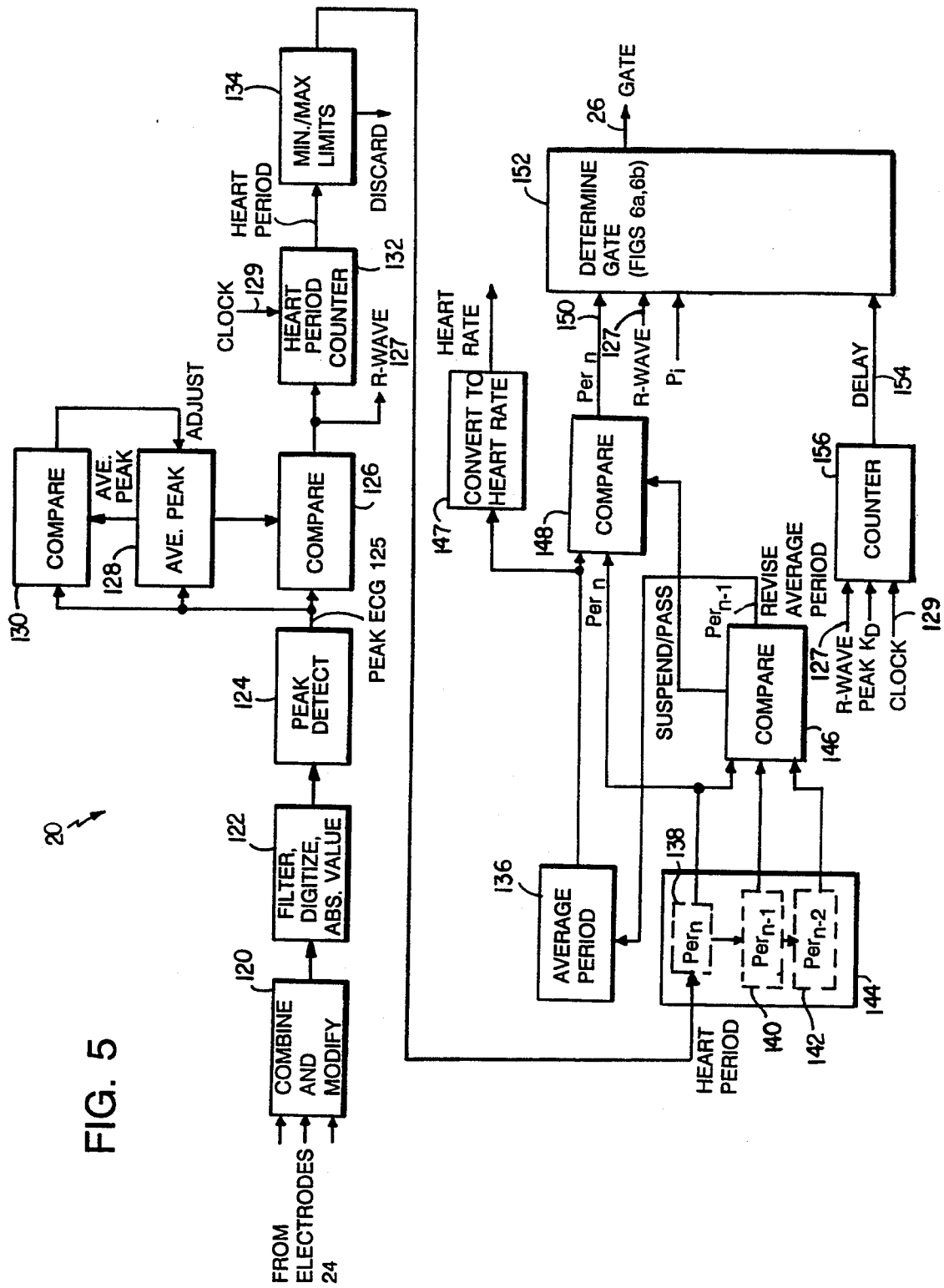
FIG. 5 illustrates the development of a cardiac gate used during the operation of the blood pressure monitor of FIG. 1.

FIG. 5 shows cardiac gating circuitry 22 in detail. The signals from cardiac electrodes 24 are combined and amplified (120). The amplification stage includes an isolated ECG amplifier that prevents potentially harmful electrical signals from equipment failure from being coupled to chest electrodes 24. During preprocessing (122) the amplified ECG signals are bandpass filtered, digitized, and the absolute values are taken to produce a series of digital words which are all positive in value. Peaks in the ECG signal are sensed by detector 124.

The peak ECG signals 125 are compared (126) to a fraction (60%) of the average of previously received peak ECG signals 128. Each peak ECG signal 125 that exceeds 60% of the average peak is deemed to represent the occurrence of an "R-wave" 127 in the heart cycle. Each peak ECG signal 125 is also compared (130) to average peak 128. If peak ECG signal 125 exceeds average peak 128, average peak 128 is increased by 3%, but if peak ECG signal 125 is less than average 128, average 128 is decreased by 4%. As a result, average peak 128 closely tracks individual peak ECG values 125.

Each detected R-wave 127 resets and starts a counter 132, which is incremented by a 60 Hz clock 129. Thus, immediately before being reset, the value of counter 132 represents the time interval between successive R-waves, that is, the heart period. The successive heart periods derived by counter 132 are compared with limits 134 that represent the minimum and maximum heart beat periods that are physiologically possible, and heart periods outside of these limits are discarded as noise.

Heart periods that are not discarded are averaged in a manner described in detail below and saved (136). The heart periods are also sequentially stored in register 144. At any one time the three most recent heart rate periods ($PER_n$, $PER_{n-1}$, and $PER_{n-2}$) are saved in order in locations 138, 140, 142. Comparator 146 compares the intermediate period ($PER_{n-1}$) with both the earlier period ($PER_{n-2}$) and the most recent period ($PER_n$). If the intermediate period is sufficiently close (e.g., within +/−20%) of both the earlier and later periods, the intermediate period is used to update average period 136. Average period 136 is converted (147) to a heart rate, which is supplied to memory 52, display 54, and printer 56 as described above.

Another comparator 148 compares the current heart period $PER_n$ to average heart period 136, and the current heart period and is accepted as valid 150 and used to generate a cardiac gate 26 if the period is within (+/−40%) of the average period. Comparator 146 determines that the patient is experiencing arrythmia if intermediate period $PER_{n-1}$ is not within +/−20% of either $PER_n$ or $PER_{n-2}$, and responds by ordering comparator 148 to suspend the average period comparison until the next heart beat. If comparator 146 determines that 15% or more of the heart periods are outside of the +/−20% limits, such as for chronically arrhythmic patients, comparator 146 directs comparator 148 to pass all periods $PER_n$ without regard to their relationship to the average period.

Figure 6A:
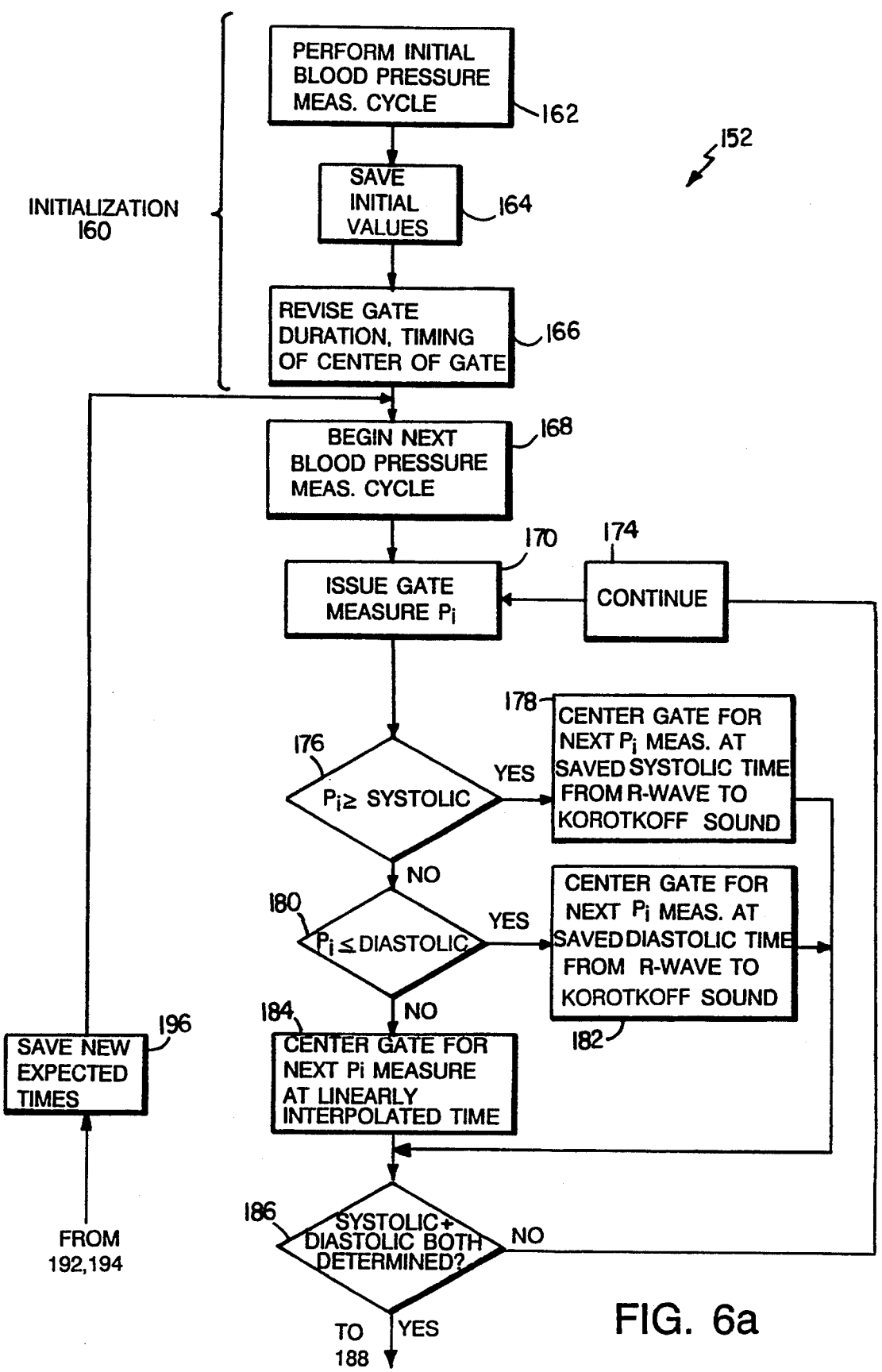
FIGS. 6a and 6b are a flow chart that shows adaptively adjusting the timing and duration of the cardiac gate during operation.
Figure 6B:
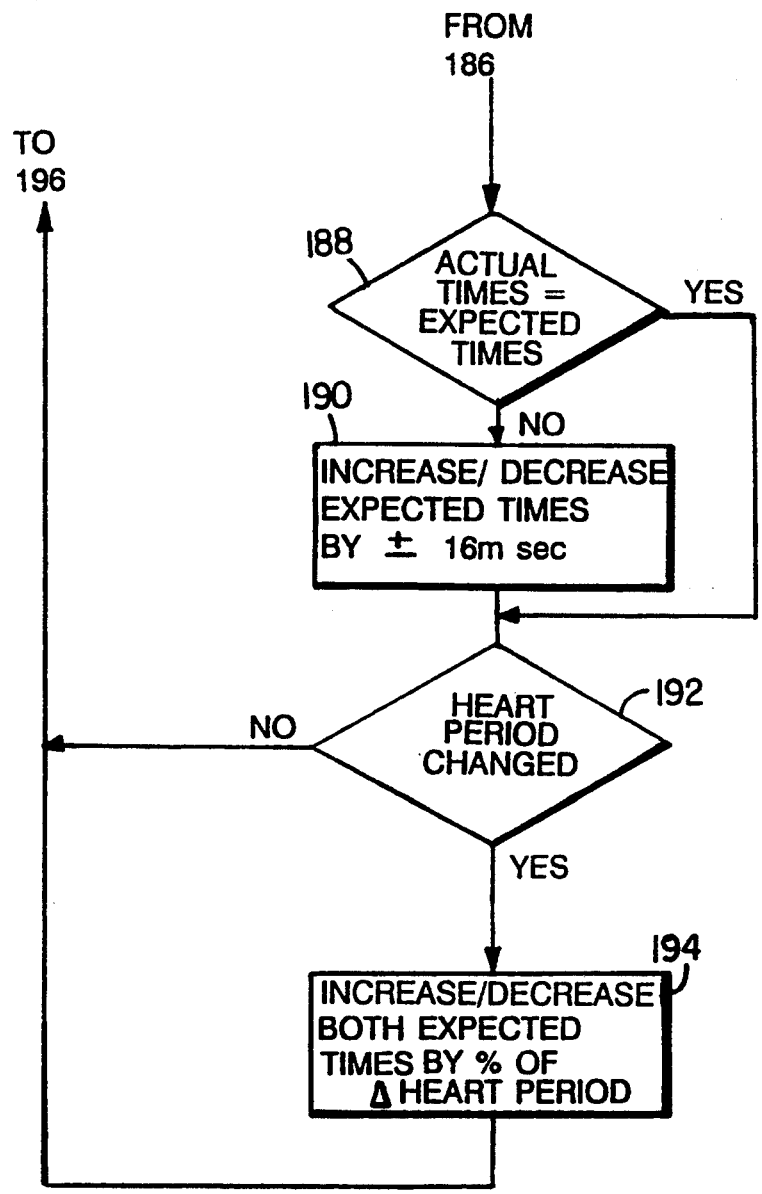

Referring also to FIG. 6, computer 30 executes a procedure 152 for predicting both the time of occurrence and the duration of each cardiac gate 26 during each blood pressure measurement cycle, and adapting the time of occurrence as cuff pressure is changed (i.e., lowered) during the cycle. In addition, the parameters used to predict the times of occurrence and durations of cardiac gates 26 in each subsequent measurement cycle are adaptively changed according to the Korotkoff sound timing and blood pressure measurements made in the previous measurement cycle. As a result, cardiac gates 26 are issued at times, and for durations, that most likely coincide with the occurrence of valid Korotkoff sounds, thereby further increasing the noise immunity of blood pressure monitor 10.

The procedure is as follows. First, blood pressure monitor 10 is initialized (step 160) by performing the initial measurement discussed above (step 162). Cuff 16 is fully inflated and then incrementally deflated after each R-wave. History thresholds 76 are set based on a predetermined value of average maximum $\overline{K_D}$ that represents the amplitude of a normal Korotkoff sound, and are updated during the initial measurement cycle based on the amplitude of the valid Korotkoff sounds detected. The initial systolic and diastolic pressures are then computed as discussed above.

The initial systolic and diastolic pressures are saved (step 164) in memory locations 96, 98, respectively (FIG. 3). Other initial values are saved (step 164) as well. They include the time delay 154, as determined by counter 156, between the R-wave 127 and the peak $K_D$ signal that corresponds to the systolic pressure, and the delay between the R-wave 127 and the peak $K_D$ signal associated with the initial diastolic pressure; these time periods are stored in memory locations 87 and 89, respectively. The peak $K_D$ signals obtained during the initial blood pressure measurement cycle are also used to revise the average maximum $\overline{K_D}$ value 80 (FIG. 3). The average heart rate during the initial measurement cycle is stored in location 97. At the conclusion of the initial blood pressure measurement cycle, computer 30 calculates initial values for the cardiac gate duration and the time during the heart cycle at which the gate will be centered. These values are stored (step 164) in memory locations 91 and 93, respectively. During the initial measurement cycle only, the cardiac gate duration is set at 50% of the value of the heart period represented by the rate stored in location 97, and the initial center time for the cardiac gate is calculated so that the gate will start immediately upon the detection of R-wave signal 127.

In advance of beginning the next measurement cycle, computer 30 revises (step 166) the duration of cardiac gate 26 to 28% of the initial gate duration value and saves the new value in location 91, replacing the old, 50% value. Computer 30 also shifts the center of gate 26 to the time delay (stored in location 87) between the R-wave 127 and the peak $K_D$ signal that corresponds to the initial systolic pressure. The revisions in the duration and timing of cardiac gate 26 are made to cause cardiac gate 26 to approximately coincide with Korotkoff sounds occurring at cuff pressures at systolic pressure and above.

The next blood pressure measurement cycle then begins (step 168), commencing at cuff pressures above the initial systolic pressure using cardiac gates 26 which occur at times designated by the value stored in location 87. The duration of each gate is 28% of the heart period that corresponds to the heart rate stored in location 97, and thus the width of gates 26 is changed during the measurement cycle according to changes in heart rate. A measurement of pressure $P_i$ is taken for each issued cardiac gate 26 and the signals produced by transducers 18, 20 during gate 26 are analyzed for the presence of Korotkoff sounds or noise in the manner described above (step 170).

Each time that cuff 16 is incrementally deflated, computer 30 determines whether the center of the next cardiac gate 26 should be shifted during the heart cycle in accordance with the current pressure of cuff 16. If the current pressure $P_i$ of cuff 16 is greater than or equal to the most recently measured systolic pressure, as saved in location 96 (step 176), the center of the next cardiac gate 26 is maintained at its current time—the time from R-wave signal 127 to peak $K_D$ signal as saved in location 87 (step 178). If the blood pressure measurement cycle has proceeded sufficiently so that cuff pressure $P_i$ equals or is less than the most recently measured diastolic pressure stored in location 98 (step 180), subsequent cardiac gates are centered at the time (saved in location 89) from R-wave signal 127 to the peak $K_D$ signal (step 182).

For intermediate pressures, the time at which the next cardiac gate 26 is centered is determined by linear interpolation (step 184). The interpolation is performed by evaluating the value of current cuff pressure $P_i$ between the most recently measured systolic and diastolic pressure values. The same relationship is applied to the difference between the R-wave-to-$K_D$ signal times for systolic and diastolic pressures (stored in locations 87 and 89) to obtain the interpolated time for the center of the next cardiac gate 26. The measurement cycle continues (174) until new systolic and diastolic pressures have been determined (step 186).

Before performing the next subsequent measurement cycle, computer 30 assesses the accuracy of the predicted R-wave-to-$K_D$ signal times stored in locations 87 and 89 based upon the actual times for systolic and diastolic pressure, respectively, and adjusts the predicted times accordingly. Specifically, each time that a $K_D$-$P_i$ pair is stored in table 94, the time delay 154 between the associated R-wave signal 127 and the peak $K_D$ signal is also stored. The peak $K_D$ signals that correspond to systolic and diastolic pressure are identified in table 94 according to the criteria described above, and their associated time delays 154 are respectively compared with the predicted times in locations 87 and 89 (step 188). If either actual time (or both times) differs from the predicted time (or times), the erroneous predicted time (or times) is correspondingly increased or decreased by 16 mSec. to reduce the error (step 190). The predicted times are each limited to minimum and maximum values that are physiologically possible, for example, 100 mSec. and 400 mSec., respectively.

Computer 30 then compares the average heart period determined during the measurement cycle with the previous (in this example, initial) heart period that corresponds to the heart rate stored in location 97 (step 192). If the heart period has changed, the values of both the systolic and diastolic predicted R-wave-to-$K_D$ signal times are adjusted by a fraction of the change in heart period (step 194). If the heart rate is below 100 beats per minute, this fraction is 25%; otherwise, the times are adjusted by only 8% of the change in heart period. Different percentages are used because the R-wave to Korotkoff sound interval does not change linearly with variations in heart rate. The direction of the adjustments corresponds to the direction (an increase or decrease) in which the heart period changed. The new times are then saved in respective memory locations 87, 89 (step 196) for use in the next measurement cycle. The entire procedure is repeated for the next and all subsequent measurement cycles.

5. Large Amplitude Noise Suspension

Referring again to FIGS. 2 and 5, excessive signal levels detected by transducers 18, 20 and electrodes 24 are more likely to be caused by noise rather than valid Korotkoff sounds or cardiac signals, respectively. Thus, each peak $K_D$ signal (from detector 74) and peak ECG signal 125 is compared with a relatively high threshold selected to represent the maximum, non-noise signal expected. The threshold is 150% of the average maximum $K_D$ used for history thresholds 76. If the threshold is exceeded by either peak signal, the blood pressure measurement is suspended and is not resumed until three seconds after the peak $K_D$ and peak ECG signals both fall below the threshold. This helps ensure that the noise has truly abated before recommencing the measurement, thereby avoiding the need for continual interruption.

A running total of the suspension periods is kept by computer 30. If the total exceeds 15 seconds in a measurement cycle, the entire cycle is aborted. Blood pressure measurement resumes in the next scheduled cycle.

6. Other Embodiments

Other embodiments are within the scope of the following claims.

Figure 7:
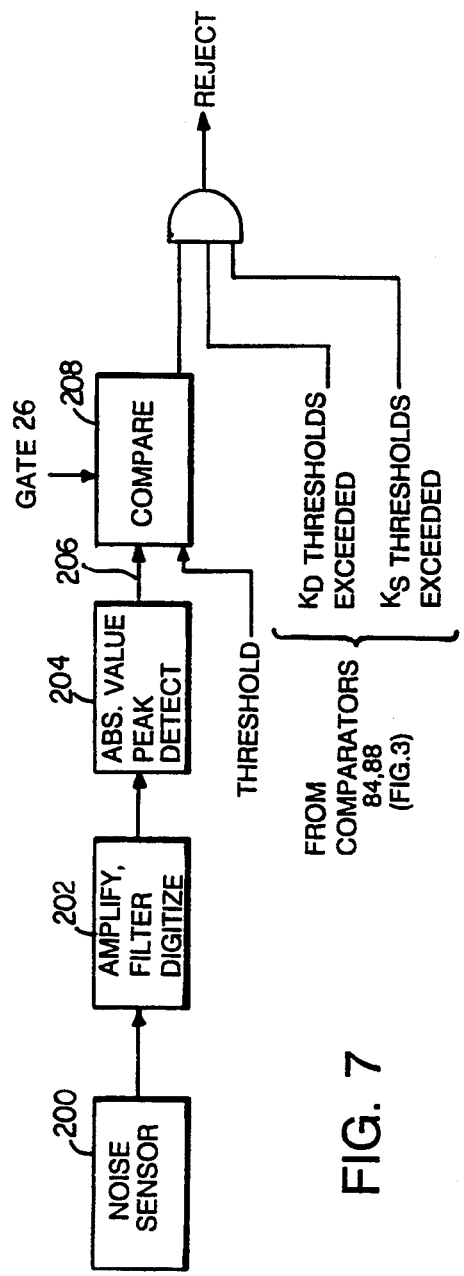
FIG. 7 shows an alternative or additional noise discrimination technique for the blood pressure monitor of FIG. 1.

For example, FIG. 7 shows a noise level detection technique useful as an alternative (or in addition) to the method shown in FIG. 4. A separate noise sensor 200 is positioned to detect noise preferentially to Korotkoff sounds. For example, sensor 200 is worn on a belt, or attached to treadmill 14 (FIG. 1), or disposed at any other location that allows sensor 200 to detect noise correlated signals (such as the patient's foot striking the treadmill).

The signals produced by sensor 200 are amplified, bandpass filtered, and digitized 202 in a similar manner as that discussed above. After the absolute values of the digital words have been taken and peak detection has been performed 204, the noise signal 206 is applied to a comparator 208 along with a predetermined threshold value that is set at the minimum acceptable level for such noise correlated events. Note that unlike the technique of FIG. 4, the comparison is made during, not outside of, cardiac gates 26.

The noise level is considered to be unacceptably high if noise signal 206 exceeds the comparison threshold. Thus, even if comparators 84, 88 (FIG. 3) respectively indicate that history thresholds 76 and noise thresholds 78 are exceeded during cardiac gate 26, the candidate Korotkoff sound is rejected 208. (This operation is represented by logic AND gate 210.) Computer 30 responds in the same manner as for any other invalid Korotkoff sound.

Figure 8:
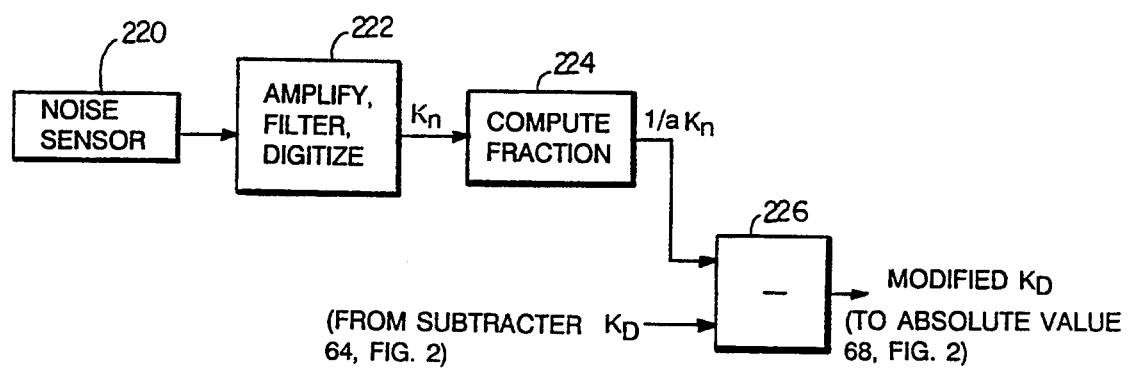
FIG. 8 shows yet another alternative or additional technique for reducing noise in the blood pressure monitor of FIG. 1.

Referring to FIG. 8, a noise sensor 220 having substantially the same sensitivity and similar frequency response as transducers 18, 20 (FIG. 1) is positioned (such as on the opposite side of cuff 16 from transducers 18, 20) to detect motion and other noise preferentially to blood pressure (e.g., Korotkoff) signals. Because of their close relative locations sensor 220 and transducers 18, 20 detect noise from the same source (such as the motion of the subject's arm or the sounds caused by the subject moving about). As a result, the noise detected by sensor 220 is somewhat correlated to that detected by transducers 18, 20, and thus can be used as a discriminant to reduce the level of noise in the $K_D$ signals from the transducers.

The electrical signals produced by noise sensor 220 are amplified, filtered, and digitized (222) in much the same manner as discussed above. A fraction (1/a) of the digitized signals ($K_n$) is then computed (224), and the fractional noise signal is applied to a subtracter together with the $K_D$ signal from subtracter 64 (FIG. 2). The fraction of $K_n$ is selected to minimize the total power in the modified $K_D$ signal produced by subtracter 226 (i.e., $[K_D-(1/a)K_n]$. Because the noise sensed by detector 220 is correlated with that detected by transducers 18, 20, the noise is significantly reduced by the subtraction. As a result, the signal to noise ratio of the modified $K_D$ signal 226 is enhanced.

The modified $K_D$ signal is applied to absolute value generator 68 (FIG. 2), and processing proceeds in the same manner as discussed above.

Techniques described above may be used with other blood pressure measuring techniques, such as the oscillometric technique and the pulse propagation method discussed above, and arterial tonometry, impedance plethysmography and ultrasonic blood flow measurement.

We claim:

1. A method for use in measuring blood pressure, comprising
   detecting a plurality of mixed signals, each of which includes biological signals indicative of blood pressure and signals not indicative of blood pressure,
   separating said signals not indicative of blood pressure from said biological signals to develop a threshold, said separating including combining said plurality of mixed signals with each other so as to reinforce said signals not indicative of blood pressure and attenuate said biological signals so that said threshold is based predominantly on a level of said signals not indicative of blood pressure that have been separated from said biological signals, and
   using said threshold to aid in discriminating said signals indicative of blood pressure from said signals not indicative of blood pressure.

2. The method of claim 1 further comprising detecting at least said signals indicative of blood pressure with a transducer.

3. The method of claim 2 further comprising using said transducer with a blood pressure cuff and wherein said signals indicative of blood pressure include signals relating to blood flow.

4. The method of claim 3 further comprising using said transducer to detect said signals indicative of blood pressure and said signals not indicative of blood pressure.

5. The method of claim 2 further comprising detecting said signals not indicative of blood pressure with said transducer.

6. The method of claim 5 further comprising using said transducer with a blood pressure cuff and wherein said signals indicative of blood pressure include signals relating to blood flow.

7. The method of claim 1 further comprising
   using said threshold to aid in said discriminating during successive cardiac cycle intervals, and
   developing said threshold for each said cardiac cycle interval based on said signals not indicative of blood pressure detected at least in part during said cardiac cycle interval.

8. The method of claim 7 further comprising developing said threshold for each said cardiac cycle interval based on said signals not indicative of blood pressure detected only during said cardiac cycle interval.

9. The method of claim 1 further comprising increasing said threshold if said signals not indicative of blood pressure exceed a predetermined level.

10. The method of claim 9 further comprising
    using said threshold to aid in said discriminating for signals occurring during a selected portion of a cardiac cycle, and
    determining whether said predetermined level is exceeded by signals occurring outside of said selected portion.

11. The method of claim 9 further comprising decreasing said threshold if said signals not indicative of blood pressure subsequently are reduced below said predetermined level.

12. The method of claim 1 further comprising
    developing a second threshold based predominantly on levels of previously detected signals indicative of blood pressure, and
    using said second threshold to further aid in discriminating said signals indicative of blood pressure from said signals not indicative of blood pressure.

13. The method of claim 12 further comprising increasing said second threshold if said signals not indicative of blood pressure exceed a predetermined level.

14. The method of claim 13 further comprising decreasing said second threshold if said signals not indicative of blood pressure subsequently are reduced below said predetermined level.

15. The method of claim 1 further comprising disposing said pair of transducers under said blood pressure cuff and inflating said cuff during said measurement.

16. A method for use in measuring blood pressure, comprising
    detecting biological signals indicative of blood pressure and signals not indicative of blood pressure,
    developing a threshold based predominantly on a level of said signals not indicative of blood pressure, using said threshold to aid in discriminating said signals indicative of blood pressure from said signals not indicative of blood pressure, increasing said threshold if said signals not indicative of blood pressure exceed a predetermined level, decreasing said threshold if said signals not indicative of blood pressure subsequently are reduced below said predetermined level, and requiring said signals not indicative of blood pressure to remain below said predetermined level for a predetermined time before decreasing said threshold.

17. A method for use in measuring blood pressure, comprising detecting biological signals indicative of blood pressure and signals not indicative of blood pressure, developing a threshold based predominantly on a level of said signals not indicative of blood pressure, using said threshold to aid in discriminating said signals indicative of blood pressure from said signals not indicative of blood pressure, developing a second threshold based predominantly on levels of previously detected signals indicative of blood pressure, using said second threshold to further aid in discriminating said signals indicative of blood pressure from said signals not indicative of blood pressure, increasing said second threshold if said signals not indicative of blood pressure exceed a predetermined level, decreasing said second threshold if said signals not indicative of blood pressure subsequently are reduced below said predetermined level and remain below said predetermined level for a predetermined time.

18. A method for use in measuring a blood pressure, comprising detecting biological signals indicative of blood pressure and signals not indicative of blood pressure with a pair of transducers and a blood pressure cuff, summing output signals generated by said pair of transducers to develop threshold based predominantly on a level of said signals not indicative of blood pressure, said output signals including both said signals indicative of blood pressure and said signals not indicative of blood pressure, and using said threshold to aid in discriminating said signals indicative of blood pressure from said signals not indicative of blood pressure.

19. The method of claim 18 further comprising determining a predetermined fraction of the sum of said output signals and using said fraction as said threshold.

20. The method of claim 19 further comprising determining said fraction based at least in part on heart rate.

21. The method of claim 19 further comprising increasing said fraction if said signals not indicative of blood pressure exceed a predetermined level.

22. The method of claim 21 further comprising using said threshold to aid said discriminating for signals occurring during a selected portion of a cardiac cycle, and determining whether said predetermined level is exceeded by signals occurring outside of said selected portion.

23. The method of claim 21 further comprising decreasing said fraction if said signals not indicative of blood pressure decrease below said predetermined level.

24. The method of claim 23 further comprising requiring said signals not indicative of blood pressure to remain below said predetermined level for a plurality of cardiac cycles before decreasing said fraction to said predetermined fraction.

25. The method of claim 18 further comprising subtracting one of said output signals from the other of said output signals to develop a candidate blood pressure signal, and comparing said candidate blood pressure signal with said threshold.

26. The method of claim 25 further comprising designating said candidate blood pressure signal as corresponding to a valid blood pressure signal if it exceeds said threshold.

27. The method of claim 18 further comprising defining a pair of areas of a single transducer to provide said pair of transducers.

28. Apparatus for use in a blood pressure measuring device, comprising means for detecting a plurality of mixed signals, each of which includes biological signals indicative of blood pressure and signals not indicative of blood pressure, means for separating said signals not indicative of blood pressure from said biological signals to develop a threshold, said means for separating including means for combining said plurality of mixed signals with each other so as to reinforce said signals not indicative of blood pressure and attenuate said biological signals so that said threshold is based predominantly on a level of said signals not indicative of blood pressure that have been separated from said biological signals, and means for using said threshold to aid in discriminating said signals indicative of blood pressure from said signals not indicative of blood pressure.

29. The apparatus of claim 28 wherein said means for detecting comprises a transducer that detects at least said signals indicative of blood pressure.

30. The apparatus of claim 28 wherein said means for detecting comprises a transducer that detects said signals indicative of blood pressure and said signals not indicative of blood pressure.

31. The apparatus of claim 30 wherein said means for detecting further comprises a blood pressure cuff and said signals indicative of blood pressure include signals relating to blood flow.

32. The apparatus of claim 28 wherein said means for using uses said threshold with said detected signals during successive cardiac cycles, and said means for developing said threshold produces a said threshold for each said cardiac cycle based on said signals not indicative of blood pressure detected at least in part during said cardiac cycle.

33. The apparatus of claim 28 further comprising means for increasing said threshold if said signals not indicative of blood pressure exceed a predetermined level.

34. The apparatus of claim 28 further comprising means for developing a second threshold based predominantly on levels of previously detected signals indicative of blood pressure, means for using said second threshold to further aid in discriminating said signals indicative of blood pressure from said signals not indicative of blood pressure, and means for increasing said second threshold if said signals not indicative of blood pressure exceed a predetermined level.

35. The apparatus of claim 34 further comprising means for increasing said second threshold if said signals not indicative of blood pressure exceed a predetermined level.

36. Apparatus for use in a blood pressure measuring device, comprising means for detecting biological signals indicative of blood pressure and signals not indicative of blood pressure, said means for detecting including a pair of transducers and a blood pressure cuff, each one of said transducers generating output signals that include both said signals indicative of blood pressure and said signals not indicative of blood pressure, means for summing said output signals to develop a threshold based predominantly on a level of said signals not indicative of blood pressure, and means for using said threshold to aid in discriminating said signals indicative of blood pressure from said signals not indicative of blood pressure.

37. The apparatus of claim 36 further comprising means for subtracting said output signals to develop a candidate blood pressure signal, and means for comparing said candidate blood pressure signal with said threshold and designating said candidate blood pressure signal as corresponding to a valid blood pressure signal if it exceeds said threshold.

38. A method for use in measuring blood pressure, comprising detecting a plurality of mixed signals, each of which includes biological signals indicative of blood pressure and signals not indicative of blood pressure, separating said signals not indicative of blood pressure from said biological signals to develop a first threshold, said separating including combining said plurality of mixed signals with each other so as to reinforce said signals not indicative of blood pressure and attenuate said biological signals so that said first threshold is based predominantly on a level of said signals not indicative of blood pressure that have been separated from said biological signals, developing a second threshold based predominantly on levels of previously detected signals indicative of blood pressure, and using said first threshold and said second threshold to aid in discriminating said signals indicative of blood pressure from said signals not indicative of blood pressure.

39. The method of claim 38 further comprising detecting at least said signals indicative of blood pressure with a transducer.

40. The method of claim 39 further comprising using said transducer to detect said signals indicative of blood pressure and said signals not indicative of blood pressure.

41. The method of claim 40 further comprising using said transducer with a blood pressure cuff and wherein said signals indicative of blood pressure include signals relating to blood flow.

42. The method of claim 38 further comprising increasing said first threshold and said second threshold if said signals not indicative of blood pressure exceed a predetermined level.

43. The method of claim 42 further comprising using said first and second thresholds to aid in said discriminating for signals occurring during a selected portion of a cardiac cycle, and determining whether said predetermined level is exceeded by signals occurring during outside of said selected portion of said cardiac cycle.

44. The method of claim 42 further comprising decreasing said first threshold and said second threshold if said signals not indicative of blood pressure subsequently are reduced below said predetermined level.

45. A method for use in measuring blood pressure, comprising detecting biological signals indicative of blood pressure and signals not indicative of blood pressure, developing a first threshold based predominantly on a level of said signals not indicative of blood pressure, developing a second threshold based predominantly on levels of previously detected signals indicative of blood pressure, and using said first threshold and said second threshold to aid in discriminating said signals indicative of blood pressure from said signals not indicative of blood pressure, increasing said first threshold and said second threshold if said signals not indicative of blood pressure exceed a predetermined level, decreasing said first threshold and said'second threshold if said signals not indicative of blood pressure subsequently are reduced below said predetermined level and remain below said predetermined level for a predetermined time.

46. A method for use in measuring blood pressure, comprising detecting biological signals indicative of blood pressure and signals not indicative of blood pressure with a pair of transducers and a blood pressure cuff, each one of said transducers producing output signals that include both said signals indicative of blood pressure and said signals not indicative of blood pressure, developing a first threshold based predominantly on a level of said signals not indicative of blood pressure, and developing a second threshold based predominantly on levels of previously detected signals indicative of blood pressure, and using said first threshold and said second threshold to aid in discriminating said signals indicative of blood pressure from said signals not indicative of blood pressure by:

subtracting one of said output signals from the other output signal to develop a candidate blood pressure signal, and comparing said candidate blood pressure signal with said first threshold and said second threshold.

47. The method of claim 46 wherein said step of developing said second threshold comprises determining an average of candidate blood pressure signals developed from said signals previously detected by said transducers.

48. The method of claim 47 wherein said step of developing said second threshold further comprises using a predetermined fraction of said average.

49. The method of claim 46 wherein said using step further includes
    comparing said second threshold to said candidate blood pressure signal and to said signals generated by each of said transducers,
    comparing said first threshold to said candidate blood pressure signal, and
    designating said candidate blood pressure signal as corresponding to a valid blood pressure signal if all of said signals exceed said thresholds.

50. The method of claim 49 further comprising
    determining an average of candidate blood pressure signals developed from said signals previously detected by said transducers, and
    using a predetermined fraction of said average as the second threshold for said candidate blood pressure signal, and using a lower fraction of said average as the second threshold for said signals generated by each of said transducers.

51. The method of claim 50 further comprising increasing said fractions if said signals not indicative of blood pressure exceed a predetermined level.

52. The method of claim 51 further comprising
    using said first and second thresholds to aid in said discriminating for signals occurring during a selected portion of a cardiac cycle, and
    determining whether said predetermined level is exceeded by signals occurring outside of said selected portion of said cardiac cycle.

53. The method of claim 51 further comprising decreasing said fractions if said signals not indicative of blood pressure subsequently are reduced below said predetermined level.

54. The method of claim 53 further comprising requiring said signals not indicative of blood pressure to remain below said predetermined level for a predetermined time before decreasing said fractions.

55. The method of claim 50 further comprising successively incrementing said fractions for cardiac cycles in which said predetermined level is exceeded, and successively decrementing said fractions for other cardiac cycles in which said predetermined level is not exceeded, said incrementing proceeding in steps that are greater than steps of said decrementing.

56. The method of claim 46 further comprising summing said signals generated by said pair of transducers to develop said first threshold.

57. The method of claim 56 wherein said using step includes
    comparing said second threshold to said candidate blood pressure signal and to said signals generated by each of said transducers,
    comparing said first threshold to said candidate blood pressure signal, and
    designating said candidate blood pressure signal as corresponding to a valid blood pressure signal if all of said signals exceed said thresholds.

58. The method of claim 56 further comprising using a predetermined fraction of the sum of said generated signals as said first threshold.

59. The method of claim 58 further comprising selecting said predetermined fraction based at least in part on heart rate.

60.

61. Apparatus for measuring blood pressure, comprising
    means for detecting a plurality of mixed signals, each of which includes biological signals indicative of blood pressure and signals not indicative of blood pressure,
    means for separating said signals not indicative of blood pressure from said biological signals to develop a first threshold, said means for separating including means for combining said plurality of mixed signals with each other so as to reinforce said signals not indicative of blood pressure and attenuate said biological signals so that said first threshold is based predominantly on a level of said signals not indicative of blood pressure that have been separated from said biological signals,
    means for developing a second threshold based predominantly on levels of previously detected signals indicative of blood pressure, and
    means for using said first threshold and said second threshold to aid in discriminating said signals indicative of blood pressure from said signals not indicative of blood pressure.

62. Apparatus for use in measuring blood pressure, comprising
    means for detecting biological signals indicative of blood pressure and signals not indicative of blood pressure, said means for detecting including a pair of transducers and a blood pressure cuff, each one of said transducers generating output signals that include said biological signals indicative of blood pressure and said signals not indicative of blood pressure,
    means for developing a first threshold based predominantly on a level of said signals not indicative of blood pressure,
    means for developing a second threshold based predominantly on levels of previously detected signals indicative of blood pressure,
    means for subtracting said output signals of one of said transducers from said output signals of another one of said transducers to develop a candidate blood pressure signal, and
    means for comparing said candidate blood pressure signal with said first threshold and said second threshold to aid in discriminating said signals indicative of blood pressure from said signals not indicative of blood pressure.

63. The apparatus of claim 62 further comprising
    means for comparing said second threshold to said candidate blood pressure signal and to said signals generated by each of said transducers,
    means for comparing said first threshold to said candidate blood pressure signal, and
    means for designating said candidate blood pressure signal as corresponding to a valid blood pressure signal if all of said signals exceed said thresholds.

64. A method for use in measuring blood pressure, comprising
    detecting, during a portion of a cardiac cycle, a plurality of mixed signals, each of which includes biological signals indicative of blood pressure and signals not indicative of blood pressure,
    separating said signals not indicative of blood pressure from said biological signals to develop a threshold, said separating including combining said plurality of mixed signals with each other so as to reinforce said signals not indicative of blood pressure and attenuate said biological signals so that said threshold is based predominantly on a level of said signals not indicative of blood pressure that have been separated from said biological signals, detecting additional signals outside said portion of said cardiac cycle, adjusting said threshold based at least in part on said additional signals, and comparing the signals detected during said portion of said cardiac cycle with said threshold as adjusted to aid in discriminating said biological signals indicative of blood pressure from said signals not indicative of blood pressure.

65. The method of claim 64 further comprising developing a threshold based at least in part on a level of said signals not indicative of blood pressure, using said threshold to further aid in discriminating said signals indicative of blood pressure from said signals not indicative of blood pressure.

66. The method of claim 65 further comprising basing said threshold at least in part on a level of said additional signals.

67. The method of claim 65 further comprising determining a nominal level for said threshold based predominantly on said level of said signals not indicative of blood pressure, and increasing said threshold from said nominal level if said additional signals exceed a predetermined level.

68. The method of claim 67 further comprising decreasing said threshold if said additional signals subsequently are reduced below said predetermined level.

69. The method of claim 65 further comprising developing a second threshold based predominantly on levels of previously detected signals indicative of blood pressure, and using said second threshold to further aid in discriminating said signals indicative of blood pressure from said signals not indicative of blood pressure.

70. The method of claim 69 further comprising basing said second threshold at least in part on a level of said additional signals.

71. The method of claim 70 further comprising increasing said second threshold if said additional signals exceed a predetermined level.

72. The method of claim 71 further comprising decreasing said second threshold if said additional signals subsequently are reduced below said predetermined level.

73. A method for use in measuring blood pressure, comprising detecting, during a portion of a cardiac cycle, biological signals indicative of blood pressure and signals not indicative of blood pressure, detecting additional signals outside said portion of said cardiac cycle, using said additional signals to aid in discriminating said signals indicative of blood pressure from said signals not indicative of blood pressure, developing a threshold based at least in part on a level of said signals not indicative of blood pressure, and determining a nominal level for said threshold based predominantly on said level of said signals not indicative of blood pressure, and using said threshold to further aid in discriminating said signals indicative of blood pressure from said signals not indicative of blood pressure, increasing said threshold from said nominal level if said additional signals exceed a predetermined level, and decreasing said threshold if said additional signals subsequently are reduced below said predetermined level and remain below said predetermined level for a predetermined time.

74. A method for use in measuring blood pressure, comprising detecting, during a portion of a cardiac cycle, biological signals indicative of blood pressure and signals not indicative of blood pressure, detecting additional signals outside said portion of said cardiac cycle, and using said additional signals to aid in discriminating said signals indicative of blood pressure from said signals not indicative of blood pressure, developing a threshold based at least in part on a level of said signals not indicative of blood pressure, using said threshold to further aid in discriminating said signals indicative of blood pressure from said signals not indicative of blood pressure, developing a second threshold based predominantly on levels of previously detected signals indicative of blood pressure and basing said second threshold at least in part on a level of said additional signals, using said second threshold to further aid in discriminating said signals indicative of blood pressure from said signals not indicative of blood pressure, increasing said second threshold if said additional signals exceed a predetermined level, and decreasing said second threshold if said additional signals subsequently are reduced below said predetermined level and remain below said predetermined level for a predetermined time.

75. A method for use in measuring blood pressure, comprising detecting, during successive portions of a cardiac cycle, a plurality of mixed signals, each of which includes biological signals indicative of blood pressure and signals not indicative of blood pressure, developing a first threshold based at least in part on a level of said signals not indicative of blood pressure, the step of developing said first threshold including combining said plurality of mixed signals with each other so as to reinforce said signals not indicative of blood pressure and attenuate said biological signals so that said first threshold is based predominantly on a level of said signals not indicative of blood pressure, developing a second threshold based predominantly on levels of previously detected signals indicative of blood pressure, using said first threshold and said second threshold to aid in discriminating said signals indicative of blood pressure from said signals not indicative of blood pressure, detecting additional signals outside said successive portions of said cardiac cycle, using said additional signals to aid in discriminating said signals indicative of blood pressure from said signals not indicative of blood pressure, incrementing, for successive portions of said cardiac cycle, said first threshold and said second threshold if said additional signals exceed a predetermined level, and subsequently decrementing, for successive portions of said cardiac cycle, said first threshold and said second threshold if said additional signals become less than said predetermined level, said incrementing proceeding in steps that are greater than steps of said decrementing.

76. The method of claim 75 further comprising establishing minimum levels below which said first-mentioned threshold and said second threshold will not be decremented.

77. Apparatus for use in a blood pressure measuring device, comprising
- means for detecting, during a portion of a cardiac cycle, a plurality of mixed signals, each of which includes biological signals indicative of blood pressure and signals not indicative of blood pressure,
- means for separating said signals not indicative of blood pressure from said biological signals to develop a threshold, said means for separating including means for combining said plurality of mixed signals with each other so as to reinforce said signals not indicative of blood pressure and attenuate said biological signals so that said threshold is based predominantly on a level of said signals not indicative of blood pressure that have been separated from said biological signals,
- means for detecting additional signals outside said portion of said cardiac cycle,
- means for adjusting said threshold based at least in part on said additional signals, and
- means for comparing the signals detected during said portion of said cardiac cycle with said threshold as adjusted to aid in discriminating said biological signals indicative of blood pressure from said signals not indicative of blood pressure.

78. A procedure for use in measuring the blood pressure of a subject by detecting a plurality of mixed signals, each of which includes biological signals indicative of blood pressure and signals not indicative of blood pressure, comprising
- a) inflating a cuff to a predetermined pressure and then decreasing said pressure in successive portions of a cardiac cycle while performing said detecting, and
- b) processing said detected signals during each portion of the cardiac cycle, said processing including
- separating said signals not indicative of blood pressure from said biological signals to develop a first threshold, said separating including combining said plurality of mixed signals with each other so as to reinforce said signals not indicative of blood pressure and attenuate said biological signals so that said first threshold is based predominantly on a level of said signals not indicative of blood pressure detected during said current portion of the cardiac cycle and that have been separated from said biological signals,
- deriving a current candidate blood pressure signal based predominantly on said signals indicative of blood pressure detected during a current portion of the cardiac cycle,
- deriving a second threshold based predominantly on candidate blood pressure signals detected during previous portions of the cardiac cycle,
- comparing said first threshold and said second threshold to said current candidate blood pressure signal to aid in discriminating said signals indicative of blood pressure from said signals not indicative of blood pressure,
- determining that a validated blood pressure signal has occurred in the current portion of the cardiac cycle if said current candidate blood pressure signal exceeds said first threshold and said second threshold,
- determining that an ambiguous signal has occurred in the current portion of the cardiac cycle if said first threshold exceeds said current candidate blood pressure signal, and
- determining that an insignificant signal has occurred in the current portion of the cardiac cycle if said second threshold exceeds said current candidate blood pressure signal.

79. The method of claim 78 further comprising
- performing said comparing during successive cardiac cycles, and
- developing said first threshold for each said cardiac cycle based predominantly on said signals not indicative of blood pressure detected during said cardiac cycle.

80. The method of claim 78 further comprising, if a validated blood pressure signal is determined to have occurred,
- storing said candidate blood pressure signal and a corresponding pressure of said cuff during said cardiac cycle, and
- incrementally decreasing said pressure and repeating said processing during a subsequent cardiac cycle.

81. The method of claim 80 further comprising discarding a validated blood pressure signal determined to have occurred in a given cardiac cycle unless another validated blood pressure signal is determined to have occurred in a next subsequent cardiac cycle.

82. The method of claim 80 further comprising
- storing candidate blood pressure signals and corresponding pressures of said cuff for each said cardiac cycle during which a validated blood pressure signal is determined to have occurred, and
- determining a systolic pressure and a diastolic pressure of the subject from said stored candidate blood pressure signals and corresponding pressures.

83. The method of claim 82 wherein said step of determining systolic pressure comprises
- comparing a third threshold to said stored candidate blood pressure signals, and
- designating as systolic pressure a highest stored pressure having a corresponding stored candidate blood pressure signal that exceeds said third threshold.

84. The method of claim 83 further comprising deriving said third threshold based on said second threshold.

85. The method of claim 84 further comprising increasing said second threshold and said third threshold if said signals not indicative of blood pressure exceed a predetermined level.

86. The method of claim 85 further comprising decreasing said second threshold and said third threshold if said signals not indicative of blood pressure subsequently are reduced below said predetermined level.

87. The method of claim 86 further comprising requiring said signals not indicative of blood pressure to remain below said predetermined level for a predetermined time before decreasing said second threshold and said third threshold.

88. The method of claim 82 further comprising rejecting said systolic pressure if it is not a predetermined amount lower than said predetermined cuff pressure.

89. The method of claim 82 further comprising, after said systolic pressure has been determined, deflating said cuff to a predetermined pressure above an expected diastolic pressure for the subject and suspending blood pressure measurements during said deflating.

90. The method of claim 82 wherein said step of determining diastolic pressure comprises identifying a stored candidate blood pressure signal determined to have occurred in a given cardiac cycle which was followed by a predetermined number of cardiac cycles in which said insignificant signals are determined to have occurred, and designating the stored pressure that corresponds to said identified blood pressure signal as said diastolic pressure.

91. The method of claim 82 further comprising comparing a third threshold to said stored candidate blood pressure signals and designating as systolic pressure a highest stored pressure having a corresponding stored candidate blood pressure signal that exceeds said third threshold, identifying a stored candidate blood pressure signal determined to have occurred in a given cardiac cycle which was followed by a predetermined number of cardiac cycles in which said insignificant signals are determined to have occurred, and designating the stored pressure that corresponds to said identified blood pressure signal as said diastolic pressure.

92. The method of claim 78 further comprising, if an ambiguous signal has occurred, maintaining said cuff pressure constant and repeating said processing during a subsequent cardiac cycle.

93. The method of claim 92 further comprising, if said ambiguous signal occurs for a predetermined number of consecutive cardiac cycles at said constant pressure, incrementally decreasing said pressure and repeating said processing during a subsequent cardiac cycle.

94. The method of claim 78 further comprising, if an insignificant signal has occurred, incrementally decreasing said cuff pressure and repeating said processing during a subsequent cardiac cycle.

95. A procedure for measuring the blood pressure of a subject by detecting a plurality of mixed signals, each of which includes biological signals indicative of blood pressure and signals not indicative of blood pressure, comprising a) inflating a cuff to a predetermined pressure and then decreasing said pressure in successive portions of a cardiac cycle while performing said detecting, b) processing said detected signals during each portion of the cardiac cycle, said processing including deriving a current candidate blood pressure signal based predominantly on said signals indicative of blood pressure detected during a current portion of the cardiac cycle, developing a first threshold by combining said plurality of mixed signals with each other so as to reinforce said signals not indicative of blood pressure and attenuate said biological signals so that said first threshold is based predominantly on a level of said signals not indicative of blood pressure detected during said current portion of the cardiac cycle, deriving a second threshold based predominantly on candidate blood pressure signals detected during previous portions of the cardiac cycle, comparing said first threshold and said second threshold to said current candidate blood pressure signal to aid in discriminating said signals indicative of blood pressure from said signals not indicative of blood pressure, determining that a validated blood pressure signal has occurred in the current portion of the cardiac cycle if said current candidate blood pressure signal exceeds said first threshold and said second threshold, determining that an ambiguous signal has occurred in the current portion of the cardiac cycle if said first threshold exceeds said current candidate blood pressure signal, and determining that an insignificant signal has occurred in the current portion of the cardiac cycle if said second threshold exceeds said current candidate blood pressure signal, c) storing candidate blood pressure signals and corresponding pressures of said cuff for each portion of said cardiac cycle during which a validated blood pressure signal is determined to have occurred, and incrementally decreasing said pressure and repeating said processing during a subsequent portion of the cardiac cycle, d) determining a systolic pressure and a diastolic pressure of the subject from said stored candidate blood pressure signals and corresponding pressures, and e) rejecting said systolic pressure if it is not within a predetermined range of pressures based on previously measured systolic pressures for the subject.

96. A procedure for measuring the blood pressure of a subject by detecting biological signals indicative of blood pressure and signals not indicative of blood pressure, comprising a) inflating a cuff to a predetermined pressure and then decreasing said pressure in successive cardiac cycles while performing said detecting, b) processing said detected signals during each cardiac cycle, said processing including deriving a current candidate blood pressure signal based predominantly on said signals indicative of blood pressure detected during a current cardiac cycle, developing a first threshold based predominantly on a level of said signals not indicative of blood pressure detected during said current cardiac cycle, deriving a second threshold based predominantly on candidate blood pressure signals detected during previous cardiac cycles, comparing said first threshold and said second threshold to said current candidate blood pressure signal to aid in discriminating said signals indicative of blood pressure from said signals not indicative of blood pressure, determining that a validated blood pressure signal has occurred in the current cardiac cycle if said current candidate blood pressure signal exceeds said first threshold and said second threshold, and, if a validated blood pressure signal is determined to have occurred, storing said candidate blood pressure signal and a corresponding pressure of said cuff during said cardiac cycle, and incrementally decreasing said pressure and repeating said processing during a subsequent cardiac cycle, determining that an ambiguous signal has occurred in the current cardiac cycle if said first threshold exceeds said current candidate blood pressure signal, and determining that an insignificant signal has occurred in the current cardiac cycle if said second threshold exceeds said current candidate blood pressure signal, c) storing candidate blood pressure signals and corresponding pressures of said cuff for each said cardiac cycle during which a validated blood pressure signal is determined to have occurred, d) determining a systolic pressure and a diastolic pressure of the subject from said stored candidate blood pressure signals and corresponding pressures, e) determining whether a current heart rate of the subject differs from a previous heart rate, and f) rejecting said systolic pressure if said systolic pressure has changed from a previously measured systolic pressure in a direction opposite to that in which said current heart rate has changed from said previous heart rate.

97. A procedure for measuring the blood pressure of a subject by detecting a plurality of mixed signals, each of which includes biological signals indicative of blood pressure and signals not indicative of blood pressure, comprising a) inflating a cuff to a predetermined pressure and then decreasing said pressure in successive portions of a cardiac cycle while performing said detecting, b) processing said detected signals during each portion of the cardiac cycle, said processing including deriving a current candidate blood pressure signal based predominantly on said signals indicative of blood pressure detected during a current portion of the cardiac cycle, developing a first threshold by combining said plurality of mixed signals with each other so as to reinforce said signals not indicative of blood pressure and attenuate said biological signals so that said first threshold is based predominantly on a level of said signals not indicative of blood pressure detected during said current portion of the cardiac cycle, deriving a second threshold based predominantly on candidate blood pressure signals detected during previous portions of the cardiac cycle, comparing said first threshold and said second threshold to said current candidate blood pressure signal to aid in discriminating said signals indicative of blood pressure from said signals not indicative of blood pressure, determining that a validated blood pressure signal has occurred in the current portion of the cardiac cycle if said current candidate blood pressure signal exceeds said first threshold and said second threshold, determining that an ambiguous signal has occurred in the current portion of the cardiac cycle if said first threshold exceeds said current candidate blood pressure signal, and determining that an insignificant signal has occurred in the current portion of the cardiac cycle if said second threshold exceeds said current candidate blood pressure signal, c) storing candidate blood pressure signals and corresponding pressures of said cuff for each portion of said cardiac cycle during which a validated blood pressure signal is determined to have occurred, and incrementally decreasing said pressure and repeating said processing during a subsequent portion of the cardiac cycle, d) determining a systolic pressure and a diastolic pressure of the subject from said stored candidate blood pressure signals and corresponding pressures, and e) said step of determining diastolic pressure comprises identifying a stored candidate blood pressure signal determined to have occurred in a given portion of the cardiac cycle which was followed by a predetermined number of cardiac cycles in which said insignificant signals are determined to have occurred, and designating the stored pressure that corresponds to said identified blood pressure signal as said diastolic pressure.

98. A procedure for measuring the blood pressure of a subject by detecting biological signals indicative of blood pressure and signals not indicative of blood pressure, comprising a) inflating a cuff to a predetermined pressure and then decreasing said pressure in successive cardiac cycles while performing said detecting, b) processing said detected signals during each cardiac cycle, said processing including deriving a current candidate blood pressure signal based predominantly on said signals indicative of blood pressure detected during a current cardiac cycle, developing a first threshold based predominantly on a level of said signals not indicative of blood pressure detected during said current cardiac cycle, deriving a second threshold based predominantly on candidate blood pressure signals detected during previous cardiac cycles, comparing said first threshold and said second threshold to said current candidate blood pressure signal to aid in discriminating said signals indicative of blood pressure from said signals not indicative of blood pressure, determining that a validated blood pressure signal has occurred in the current cardiac cycle if said current candidate blood pressure signal exceeds said first threshold and said second threshold, and, if a validated blood pressure signal is determined to have occurred, storing said candidate blood pressure signal and a corresponding pressure of said cuff during said cardiac cycle, and incrementally decreasing said pressure and repeating said processing during a subsequent cardiac cycle, determining that an ambiguous signal has occurred in the current cardiac cycle if said first threshold exceeds said current candidate blood pressure signal, and determining that an insignificant signal has occurred in the current cardiac cycle if said second threshold exceeds said current candidate blood pressure signal, c) storing candidate blood pressure signals and corresponding pressures of said cuff for each said cardiac cycle during which a validated blood pressure signal is determined to have occurred, d) determining a systolic pressure and a diastolic pressure of the subject from said stored candidate blood pressure signals and corresponding pressures by:
  comparing a third threshold to said stored candidate blood pressure signals and designating as systolic pressure a highest stored pressure having a corresponding stored candidate blood pressure signal that exceeds said third threshold,
  identifying a stored candidate blood pressure signal determined to have occurred in a given cardiac cycle which was followed by a predetermined number of cardiac cycles in which said insignificant signals are determined to have occurred,
  designating the stored pressure that corresponds to said identified blood pressure signal as said diastolic pressure, and
  increasing said third threshold if said signals not indicative of blood pressure exceed a predetermined level, and changing said designated systolic pressure and said designated diastolic pressure based on increases in said third threshold.

99. The method of claim 98 further comprising limiting amounts by which said designated systolic pressure and said designated diastolic pressure are changed.

100. A computer assisted method of measuring the blood pressure of a subject, comprising
  scheduling periodic measurement cycles;
  measuring blood pressure during each measurement cycle by:
    a) simultaneously detecting a plurality of mixed signals, each of which includes biological signals indicative of blood pressure and signals not indicative of blood pressure, and
    b) processing said detected signals to determine said blood pressure, said processing including:
      (1) separating said signals not indicative of blood pressure from said biological signals indicative of blood pressure during each measurement cycle to develop a first threshold, said separating including combining said plurality of mixed signals with each other so as to reinforce said signals not indicative of blood pressure and attenuate said biological signals so that said first threshold is based predominantly on a level of said signals not indicative of blood pressure that have been separated from said biological signals, and determining a second threshold based on said first threshold; and
      (2) using said first threshold to aid in discriminating said signals indicative of blood pressure from said signals not indicative of blood pressure; and
  suspending said measuring during one of said measurement cycles if said second threshold exceeds a predetermined level during said cycle.

101. The method of claim 100 further comprising resuming said measuring during said cycle if said signals not indicative of blood pressure subsequently become less than said predetermined level.

102. The method of claim 101 further comprising delaying resuming said measuring for a predetermined time after said signals not indicative of blood pressure become less than said predetermined level, and resuming said measuring only if said signals not indicative of blood pressure remain below said predetermined level for said predetermined time.

103. The method of claim 100 further comprising accumulating a time during said measurement cycle during which said measuring is suspended, and terminating said measurement cycle if said time exceeds a predetermined time.

104. The method of claim 101 further comprising resuming said measuring during a subsequent measurement cycle.

105. The method of claim 100 further comprising using a cuff that includes at least one transducer for performing said detecting, and
  determining said predetermined level based at least in part on levels of said signals detected by said transducer.

106. A computer assisted method of measuring the blood pressure of a subject, comprising
  scheduling periodic measurement cycles;.
  measuring blood pressure during each measurement cycle by:
    a) detecting biological signals indicative of blood pressure and signals not indicative of blood pressure using a cuff that includes at least one transducer, and
    b) processing said detected signals to determine said blood pressure;
  determining a level of said signals not indicative of blood pressure during each measurement cycle;
  suspending said measuring during one of said measurement cycles if said signals not indicative of blood pressure exceed a predetermined level during said cycle, and determining said predetermined level based at least in part on levels of said signals detected by said transducer,
  determining an average level of said biological signals that have been detected by said transducer, and
  designating said predetermined level as a predetermined fraction of said average level.

107. A computer assisted method of measuring the blood pressure of a subject, comprising
  scheduling periodic measurement cycles;
  measuring blood pressure during each measurement cycle by:
    a) detecting biological signals indicative of blood pressure and signals not indicative of blood pressure, and
    b) processing said detected signals to determine said blood pressure;
  determining a level of said signals not indicative of blood pressure during each measurement cycle;
  suspending said measuring during one of said measurement cycles if said signals not indicative of blood pressure exceed a predetermined level during said cycle; and
  determining said predetermined level based at least in part on levels of signals detected during measurement of another function of the subject during said blood pressure measurement.

108. The method of claim 107 wherein said function is heart activity and said signals are produced by at least one electrode positioned to detect cardiac signals.

109. Apparatus for measuring the blood pressure of a subject, comprising
  means for scheduling periodic measurement cycles and for measuring blood pressure during each measurement cycle, including:
    a) means for simultaneously detecting a plurality of mixed signals, each of which includes biological signals indicative of blood pressure and signals not indicative of blood pressure, and b) means for processing said detected signals to determine said blood pressure, said processing including:
  (1) means for separating said signals not indicative of blood pressure from said biological signals indicative of blood pressure during each measurement cycle to develop a first threshold, said means for separating including means for combining said plurality of mixed signals with each other so as to reinforce said signals not indicative of blood pressure and attenuate said biological signals so that said first threshold is based predominantly on a level of said signals not indicative of blood pressure that have been separated from said biological signals;
  (2) means for determining a second threshold based on said first threshold; and
  (3) means for using said first threshold to aid in discriminating said signals indicative of blood pressure from said signals not indicative of blood pressure; and
means for suspending said measuring during one of said measurement cycles if said second threshold exceeds a predetermined level during said cycle.

110. A method of measuring blood pressure, comprising
inflating a cuff to a predetermined pressure and then successively decreasing said pressure,
detecting biological signals indicative of blood pressure and signals not indicative of blood pressure,
processing said detected signals at selected times during successive cardiac cycles to determine said blood pressure, and
selecting said times based at least in part on the pressure of said cuff and in accordance with at least one component of said blood pressure being measured.

111. The method of claim 110 wherein said at least one component includes systolic pressure and diastolic pressure.

112. A method of measuring blood pressure, comprising
inflating a cuff to a predetermined pressure and then successively decreasing said pressure,
detecting biological signals indicative of blood pressure and signals not indicative of blood pressure,
processing said detected signals at selected times during successive cardiac cycles to determine said blood pressure, and
selecting said times based at least in part on the pressure of said cuff and based on a relationship between said pressure of said cuff and a previously measured systolic pressure and diastolic pressure.

113. The method of claim 112 further comprising determining whether said pressure of said cuff exceeds said previously measured systolic pressure, and
if so, selecting said time in accordance with a time that corresponds to said previously measured systolic pressure.

114. The method of claim 113 further comprising determining whether said pressure of said cuff is less than said previously measured diastolic pressure, and
if so, selecting said time in accordance with a time that corresponds to said previously measured diastolic pressure.

115. The method of claim 112 further comprising determining whether said pressure of said cuff is between said previously measured systolic pressure and said previously measured diastolic pressure, and
if so, selecting said time in accordance with a first time that corresponds to said previously measured systolic pressure and a second time that corresponds to said previously measured diastolic pressure.

116. The method of claim 115 further comprising selecting said time by linearly interpolating between said first time and said second time based on said pressure of said cuff and said previously measured systolic pressure and diastolic pressure.

117. A method of measuring blood pressure, comprising
performing a plurality of measurement cycles;
measuring blood pressure during a current measurement cycle by:
  a) detecting biological signals indicative of blood pressure and signals not indicative of blood pressure, and
  b) processing said detected signals at selected times during successive cardiac cycles that occur during said current measurement cycle to determine said blood pressure; and
selecting the times during successive cardiac cycles at which the detected signals will be processed during a succeeding measurement cycle based at least in part on said biological signals that were detected during said current measurement cycle.

118. The method of claim 117 wherein each one of said times represents a time delay between a predetermined event in a cardiac cycle and a timing signal representing said signals indicative of blood pressure, and further comprising
determining, for the current measurement cycle, said time delays that correspond to systolic blood pressure and diastolic blood pressure, and
selecting said times for said succeeding measurement cycle based on said time delays.

119. The method of claim 118 further comprising changing said times for said succeeding measurement cycle if said time delays differ from the times used during the current measurement cycle.

120. The method of claim 118 further comprising selecting said times for said successive measurement cycle based on changes in heart rate of the subject.

121. Apparatus for measuring blood pressure, comprising
means for performing a plurality of measurement cycles and for measuring blood pressure during a current measurement cycle, including:
  a) means for detecting biological signals indicative of blood pressure and signals not indicative of blood pressure, and
  b) means for processing said detected signals at selected times during successive cardiac cycles that occur during said current measurement cycle to determine said blood pressure; and
means for selecting the times during successive cardiac cycles at which the detected signals will be processed during a succeeding measurement cycle based at least in part on said biological signals that were detected during said current measurement cycle.

* * * * *

UNITED STATES PATENT AND TRADEMARK OFFICE
CERTIFICATE OF CORRECTION

PATENT NO. : 5,392,781
DATED : February 28, 1995
INVENTOR(S) : Patrick G. Phillipps et al It is certified that error appears in the above-indentified patent and that said Letters Patent is hereby corrected as shown below:

Col. 12, line 18, insert --$\bar{K}_D$ before value--.

Col. 24, line 33, delte "," after "said" (second occurrence).

Col. 25, line 68, after "60." insert --The method of claim 46 further comprising defining a pair of areas of a single transducer to provide said pair of transducers.--

Signed and Sealed this

Seventeenth Day of October, 1995

Attest:

BRUCE LEHMAN

Attesting Officer     Commissioner of Patents and Trademarks